(12) United States Patent
O'Flynn

(10) Patent No.: US 11,129,961 B2
(45) Date of Patent: Sep. 28, 2021

(54) TELESCOPIC URINARY CATHETER ASSEMBLIES

(71) Applicant: Hollister Incorporated, Libertyville, IL (US)

(72) Inventor: Padraig M. O'Flynn, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 964 days.

(21) Appl. No.: 15/565,255

(22) PCT Filed: Apr. 18, 2016

(86) PCT No.: PCT/US2016/028072
§ 371 (c)(1),
(2) Date: Oct. 9, 2017

(87) PCT Pub. No.: WO2016/182695
PCT Pub. Date: Nov. 17, 2016

(65) Prior Publication Data
US 2018/0071486 A1    Mar. 15, 2018

Related U.S. Application Data

(60) Provisional application No. 62/160,678, filed on May 13, 2015.

(51) Int. Cl.
*A61M 25/01*    (2006.01)
*A61M 25/06*    (2006.01)
*A61M 25/00*    (2006.01)

(52) U.S. Cl.
CPC .... *A61M 25/0102* (2013.01); *A61M 25/0017* (2013.01); *A61M 25/0662* (2013.01);
(Continued)

(58) Field of Classification Search
CPC .......... A61M 25/0102; A61M 25/0017; A61M 25/0662; A61M 25/002; A61M 2025/0175; A61M 2210/1085; A61M 2210/1096
(Continued)

(56) References Cited

U.S. PATENT DOCUMENTS 3,706,307 A * 12/1972 Hasson ................ A61B 5/1076
600/591
4,155,364 A    5/1979 Boxer
(Continued)

FOREIGN PATENT DOCUMENTS

EP    1 807 141 B1    5/2014
EP    2 407 201 B1    5/2014
(Continued)

OTHER PUBLICATIONS

International Search Report and Written Opinion for PCT/US2016/028072 dated Jul. 13, 2016.

*Primary Examiner* — Andrew J Mensh
(74) *Attorney, Agent, or Firm* — Cook Alex Ltd.

(57) ABSTRACT

A urinary catheter assembly includes a catheter member and a sleeve member receiving at least a portion of the catheter member and having a greater flexibility than the catheter member. The assembly also includes a stylet having a proximal end movably positioned within the catheter member, with a distal portion of the stylet being positioned outside of the catheter member. The assembly is movable between a compact configuration and an extended configuration. In the compact configuration, the distal portion of the stylet is positioned outside of the catheter member and at least partially within the sleeve member. In the extended configuration, a larger distal portion of the stylet is positioned outside of the catheter member than in the compact configuration. The assembly may be in the extended con-
(Continued)

figuration for introduction into a urethra or may be advanced through a urethra prior to being moved to the extended configuration.

20 Claims, 6 Drawing Sheets

(52) U.S. Cl.
CPC ... *A61M 25/002* (2013.01); *A61M 2025/0175* (2013.01); *A61M 2210/1085* (2013.01); *A61M 2210/1096* (2013.01)

(58) Field of Classification Search
USPC .......................................................... 604/544
See application file for complete search history.

(56) References Cited

U.S. PATENT DOCUMENTS

| | | | |
|---|---|---|---|
| 4,456,000 A | | 6/1984 | Schjeldahl et al. |
| 4,632,668 A | | 12/1986 | Wilson, Jr. et al. |
| 4,652,259 A | * | 3/1987 | O'Neil .............. A61M 25/0111 |
| | | | 600/581 |
| 5,273,052 A | * | 12/1993 | Kraus ............. A61M 25/09041 |
| | | | 600/585 |
| 5,681,274 A | | 10/1997 | Perkins et al. |
| 6,248,100 B1 | | 6/2001 | de Toledo et al. |
| 6,837,871 B2 | | 1/2005 | Gonzales et al. |
| 6,852,105 B2 | | 2/2005 | Bolmsjo et al. |
| 6,902,146 B1 | | 6/2005 | Elliott |
| 7,041,090 B2 | | 5/2006 | Bolmsjo et al. |
| 7,670,331 B2 | | 3/2010 | Tanghoej |
| 7,731,676 B2 | | 6/2010 | Maeda |
| 8,123,739 B2 | | 2/2012 | McQueen et al. |
| 8,251,955 B2 | | 8/2012 | Mittermeyer et al. |
| 8,292,873 B2 | | 10/2012 | Mickley et al. |
| 2003/0018293 A1 | | 1/2003 | Tanghoej et al. |
| 2005/0049575 A1 | | 3/2005 | Snell et al. |
| 2005/0049576 A1 | * | 3/2005 | Snell .................. A61M 27/008 |
| | | | 604/544 |
| 2005/0148999 A1 | * | 7/2005 | Beaufore .......... A61M 25/0017 |
| | | | 604/544 |
| 2006/0058737 A1 | * | 3/2006 | Herweck ............... A61M 25/00 |
| | | | 604/164.01 |
| 2006/0163097 A1 | * | 7/2006 | Murray .................. B65D 81/22 |
| | | | 206/364 |
| 2006/0253104 A1 | | 11/2006 | Pandey et al. |
| 2010/0211050 A1 | | 8/2010 | Luther |
| 2011/0224653 A1 | | 9/2011 | Torstensen |
| 2012/0271281 A1 | | 10/2012 | Schertiger |
| 2013/0035628 A1 | * | 2/2013 | Garrison ............. A61M 60/268 |
| | | | 604/8 |
| 2013/0218136 A1 | | 8/2013 | Tanghoej et al. |
| 2013/0289537 A1 | | 10/2013 | Schertiger et al. |
| 2014/0066904 A1 | | 3/2014 | Young |
| 2014/0107622 A1 | | 4/2014 | Carrillo, Jr. et al. |
| 2014/0163367 A1 | | 6/2014 | Eskuri |
| 2014/0276661 A1 | * | 9/2014 | Hannon ............. A61M 25/0113 |
| | | | 604/544 |

FOREIGN PATENT DOCUMENTS

| | | |
|---|---|---|
| GB | 507074 | 6/1939 |
| WO | WO 00/67647 | 11/2000 |
| WO | WO 2004/112878 A1 | 12/2004 |
| WO | WO 2004/112879 A1 | 12/2004 |

* cited by examiner

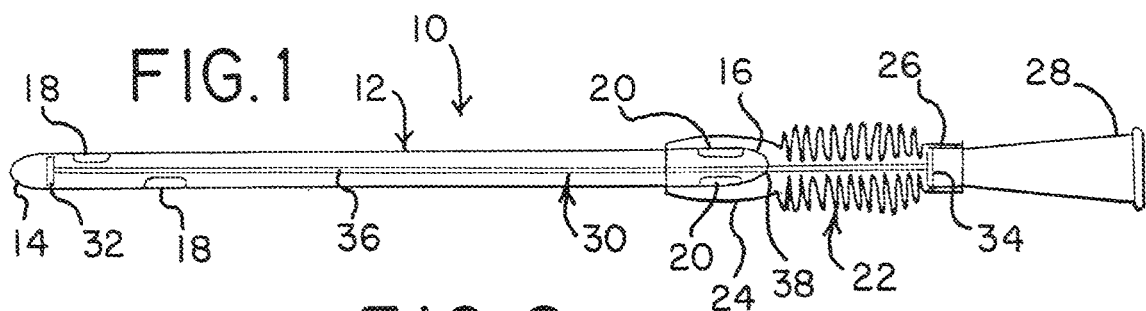
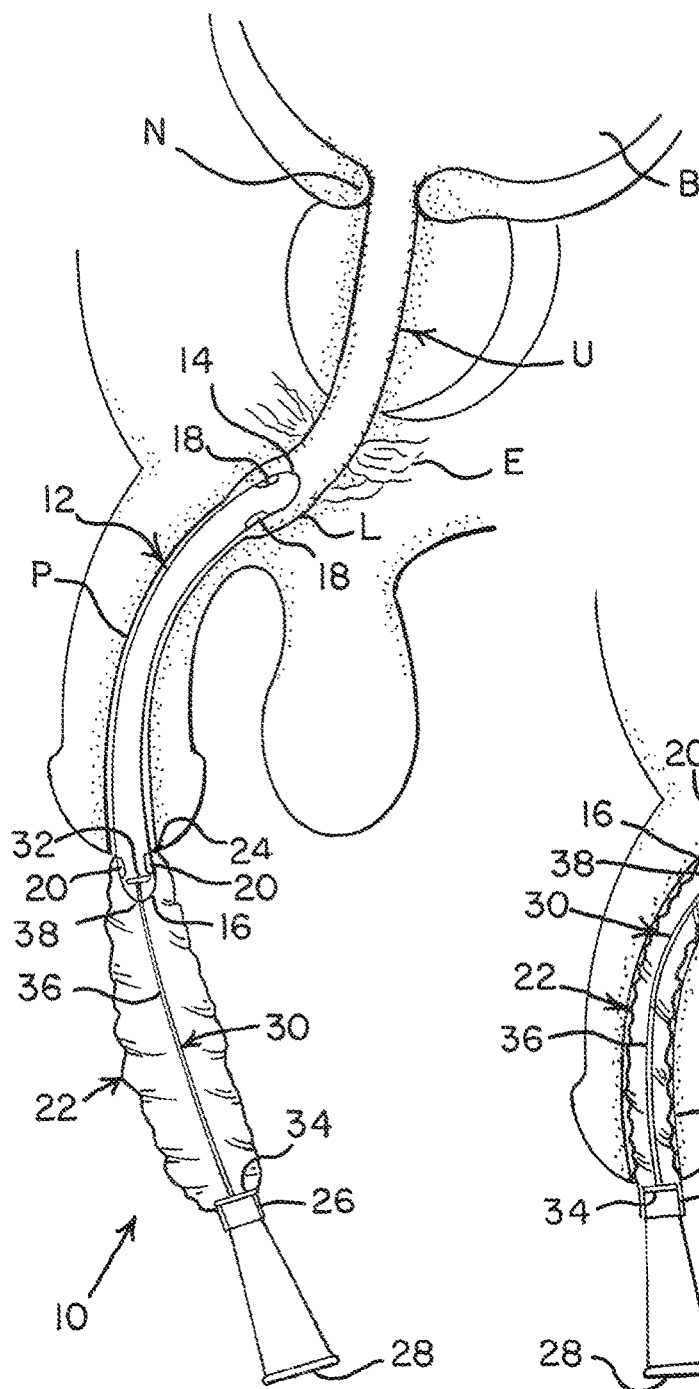
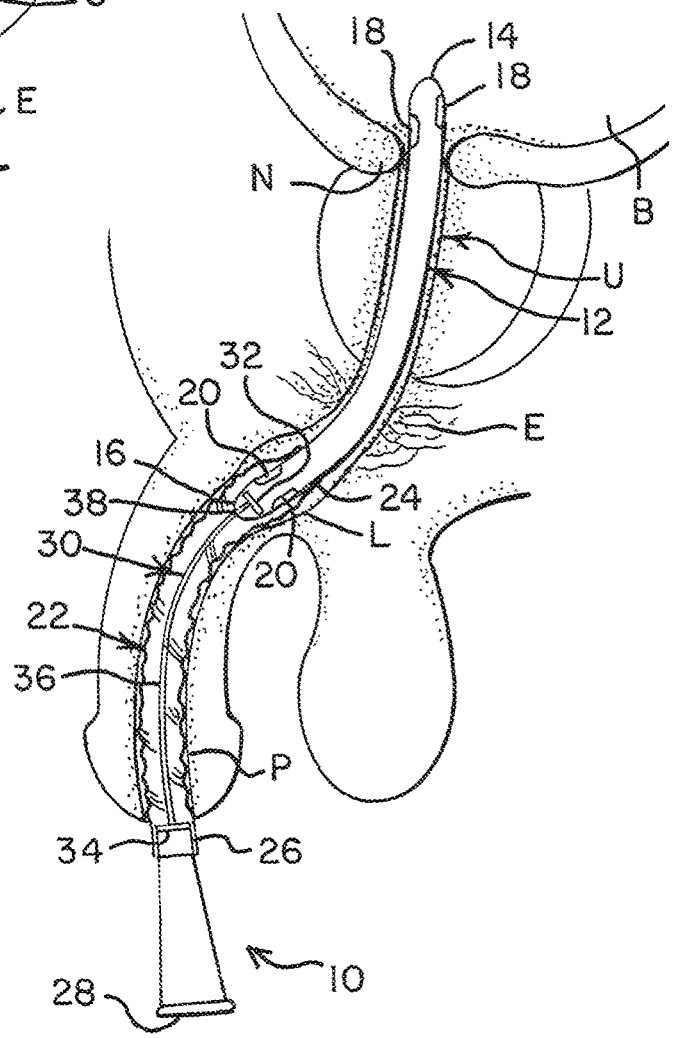

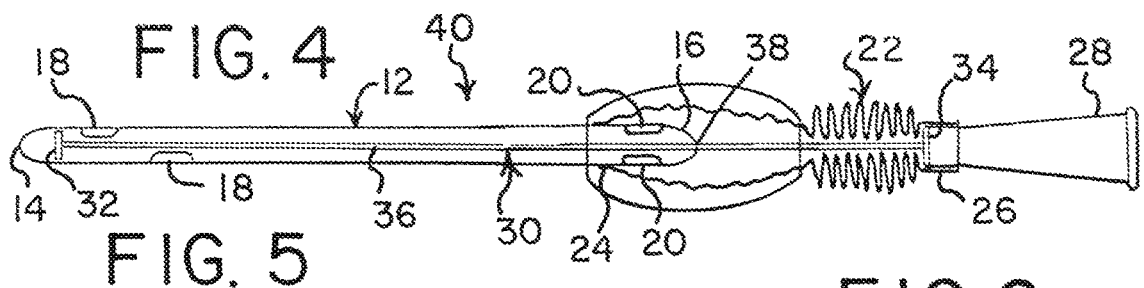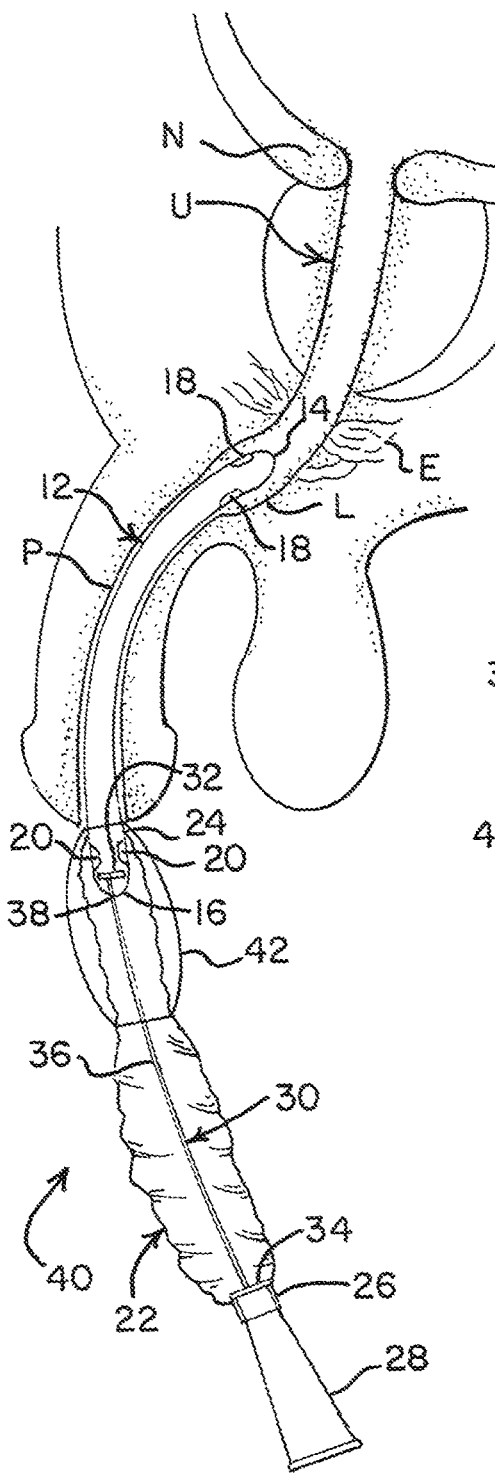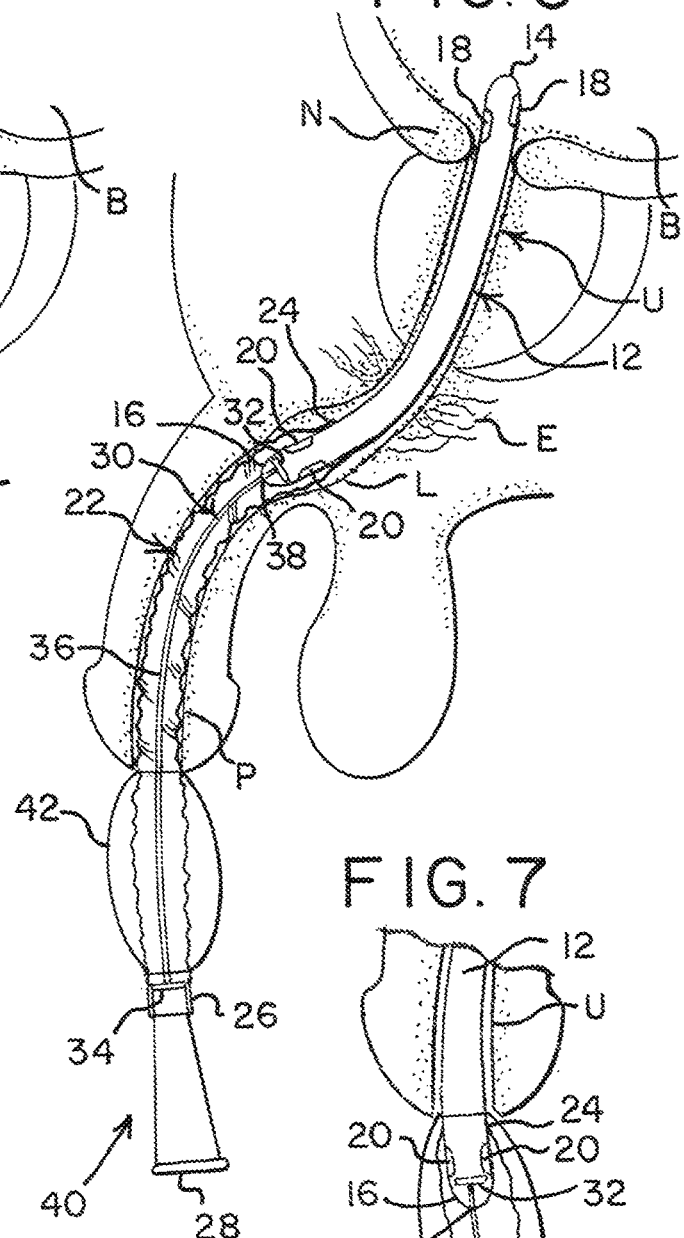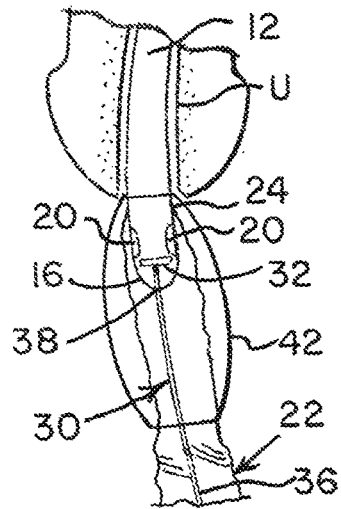

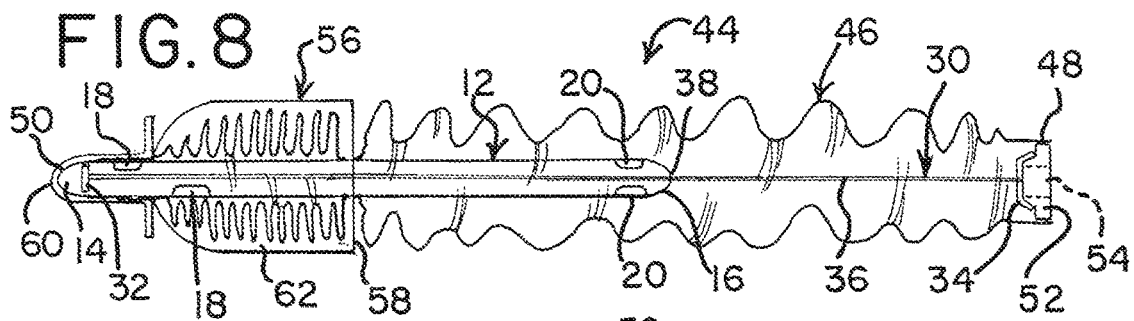
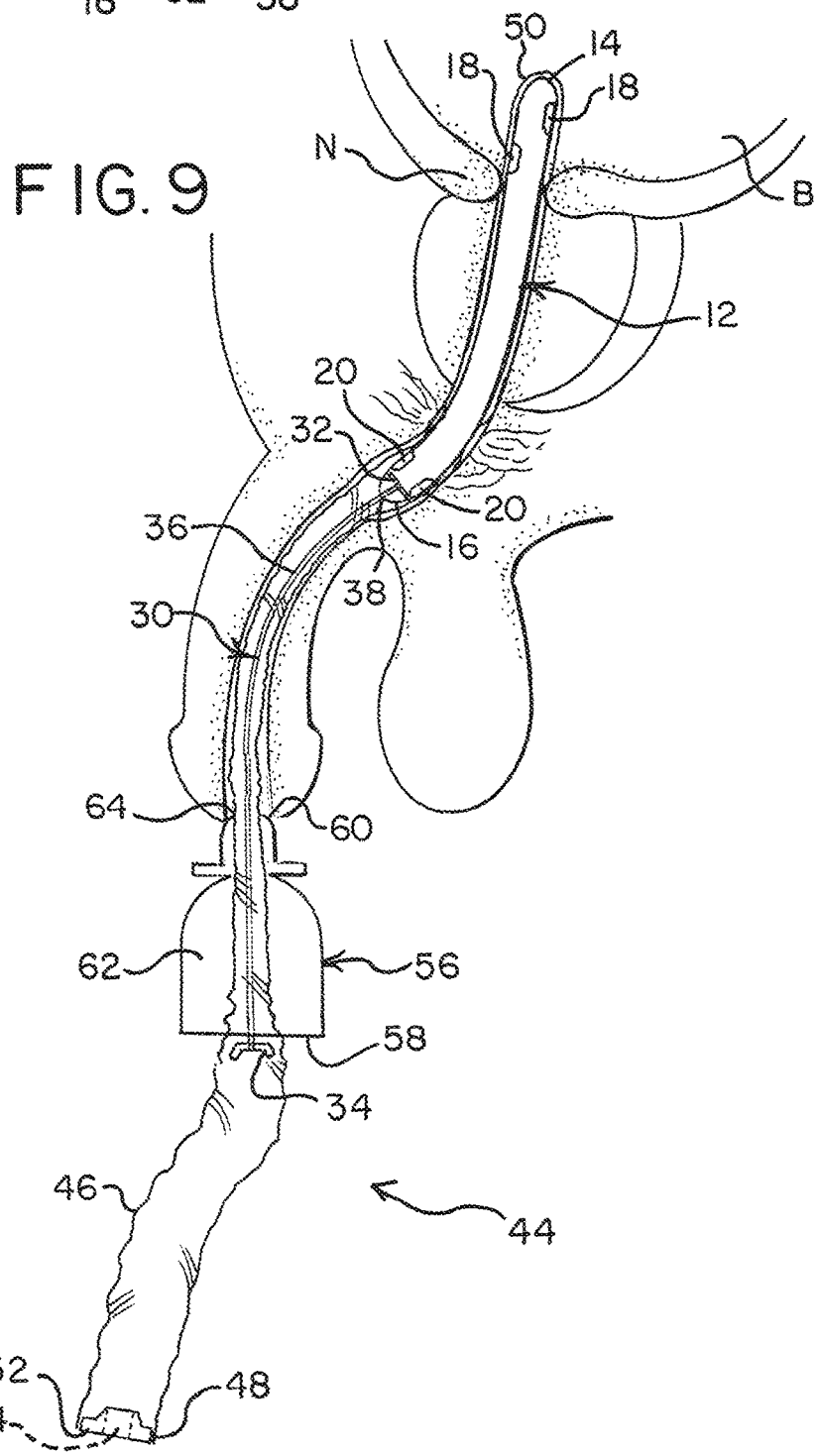

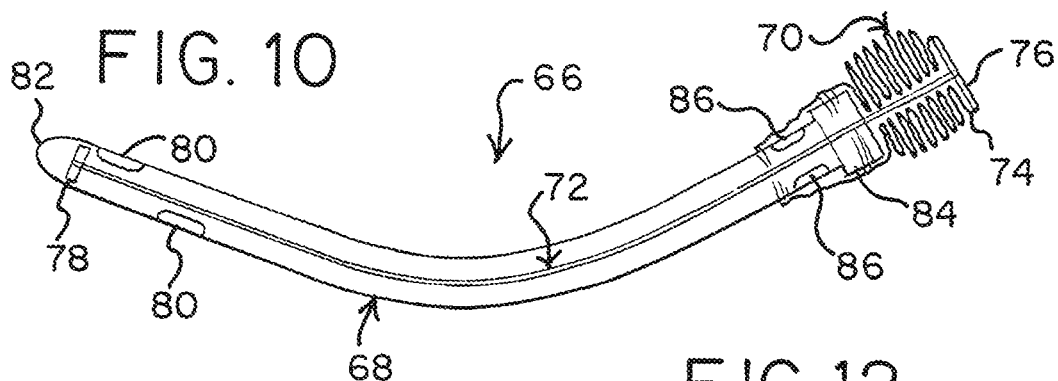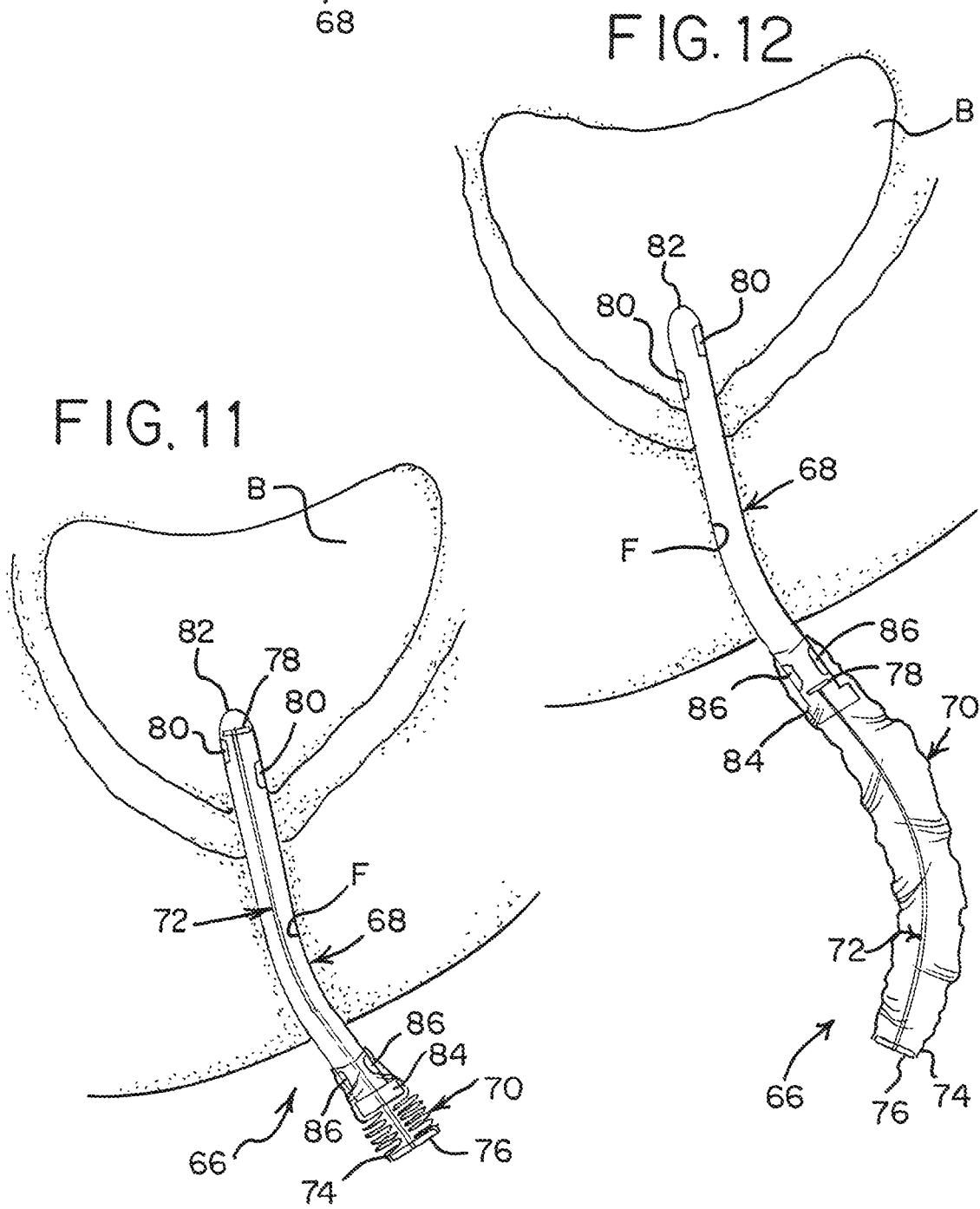

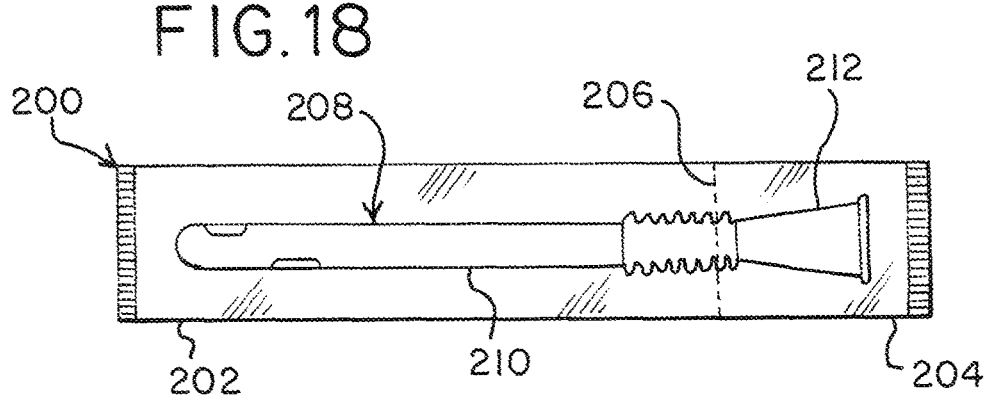
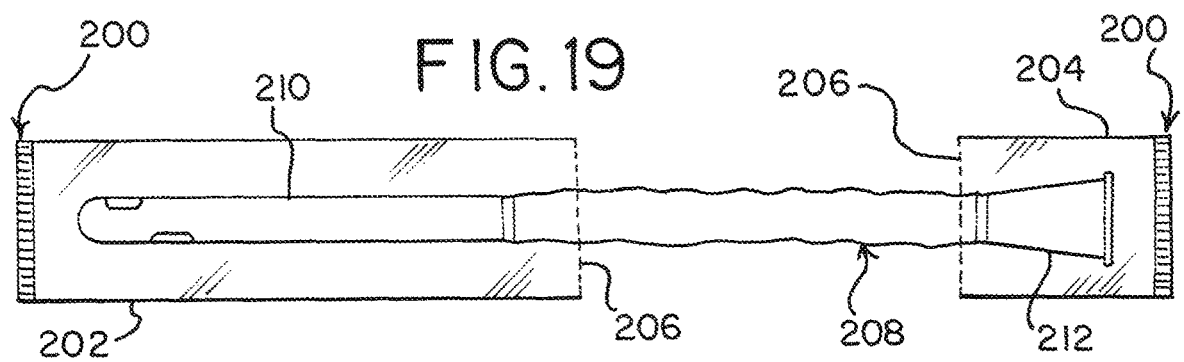
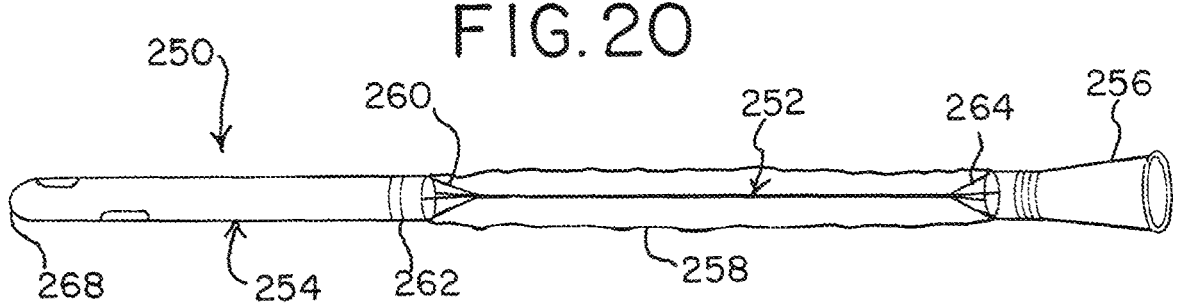
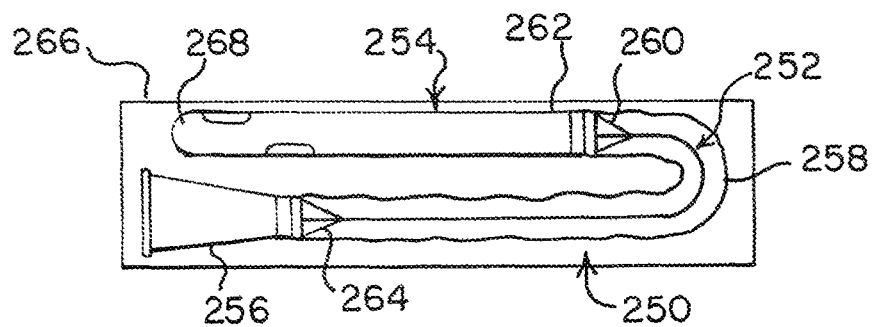

TELESCOPIC URINARY CATHETER ASSEMBLIES

RELATED APPLICATIONS

This application is a U.S. national stage application of PCT Patent Application Serial No. PCT/US2016/028072, filed Apr. 18, 2016, which claims the benefit of and priority of U.S. Provisional Patent Application Ser. No. 62/160,678, filed May 13, 2015, the contents of which are incorporated by reference herein.

DESCRIPTION

Technical Field

The present disclosure is directed to urinary catheter assemblies. More particularly, the present disclosure is directed to telescopic urinary catheter assemblies.

BACKGROUND

Intermittent catheterization is a good option for many users who suffer from various abnormalities of the urinary system. Such catheters are typically provided as single use, individually packaged items and may include a gel-lubricant or hydrophilic coating as a lubricant for reducing friction during insertion into the urethra. With the advent of intermittent urinary catheters, individuals with problems associated with the urinary system can conveniently self-catheterize to drain the individual's bladder. Individuals who suffer from urinary incontinence will self-catheterize several times a day.

Self-catheterization involves removing the catheter assembly from its package and inserting and advancing the catheter tube through the urethra. Users of intermittent catheters are often required to self-catheterize outside the privacy of the home, such as in public restrooms. Thus, for these and other reasons, it is desirable that intermittent catheters are provided in discrete packaging that is easy to open, compact and portable, and easy to dispose. Inasmuch as the male urethra is much longer than the female urethra, male catheters typically include a catheter tube that is likewise much longer than the catheter tube of a female intermittent catheter, making the compactness and portability of such catheters more challenging.

Thus, it would be desirable to provide a compact intermittent urinary catheter that, at the time of use, can be extended and advanced into the male urethra. Extendable intermittent urinary catheters for use in a female urethra would also be desirable.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a urinary catheter assembly includes a catheter member and a sleeve member receiving at least a portion of the catheter member and having a greater flexibility than the catheter member. The assembly also includes a stylet having a proximal end movably positioned within the catheter member, with a distal portion of the stylet being positioned outside of the catheter member. The assembly is movable between a compact configuration and an extended configuration.

In another aspect, a method is provided for using a urinary catheter assembly. According to the method, a urinary catheter assembly having a catheter member, sleeve member, and stylet is provided. The sleeve member receives at least a portion of the catheter member, while a proximal end of the stylet is movably positioned within the catheter member. A distal portion of the stylet is positioned outside of the catheter member and at least partially within the sleeve member. The stylet is moved distally with respect to the catheter member to position a larger distal portion of the stylet outside of the catheter member. A proximal end of the catheter member is advanced into a urethra until the proximal end of the catheter member is positioned within a bladder, with at least a distal end of the sleeve member and a distal end of the stylet positioned outside of the urethra.

In yet another aspect, a urinary catheter assembly includes a catheter member, a drainage member, and a sleeve member secured to the catheter member and drainage member. The assembly further includes a stylet positioned within the sleeve member and including a proximal end secured to the catheter member and a distal end secured to the drainage member.

BRIEF DESCRIPTION OF THE DRAWINGS

FIG. 1 is a front elevational view of an embodiment of a urinary catheter assembly in accordance with the present disclosure;

FIGS. 2 and 3 illustrate a method of advancing the urinary catheter assembly of FIG. 1 into and through a male urethra;

FIG. 4 is a front elevational view of another embodiment of a urinary catheter assembly in accordance with the present disclosure;

FIGS. 5 and 6 illustrate a method of advancing the urinary catheter assembly of FIG. 4 through a male urethra;

FIG. 7 is a detail view of a gripper member of the urinary catheter assembly of FIG. 1, with the urinary catheter assembly in the position of FIG. 5;

FIG. 8 is a front elevational view of another embodiment of a urinary catheter assembly in accordance with the present disclosure;

FIG. 9 illustrates the urinary catheter assembly of FIG. 8, fully advanced into and through a male urethra;

FIG. 10 is a front elevational view of another embodiment of a urinary catheter assembly in accordance with the present disclosure;

FIGS. 11 and 12 illustrate a method of advancing the urinary catheter assembly of FIG. 10 through a female urethra;

FIG. 18 is a front elevational view of a packaged urinary catheter assembly;

FIG. 19 is a front elevational view of the packaged urinary catheter assembly of FIG. 18, with the package in an opened or unsealed condition;

FIG. 20 is a front elevational view of another embodiment of a urinary catheter assembly in accordance with the present disclosure; and FIG. 21 is a front elevational view of the urinary catheter assembly of FIG. 20, in a compact configuration within a package.

DETAILED DESCRIPTION OF THE ILLUSTRATED EMBODIMENTS

Figure 13:
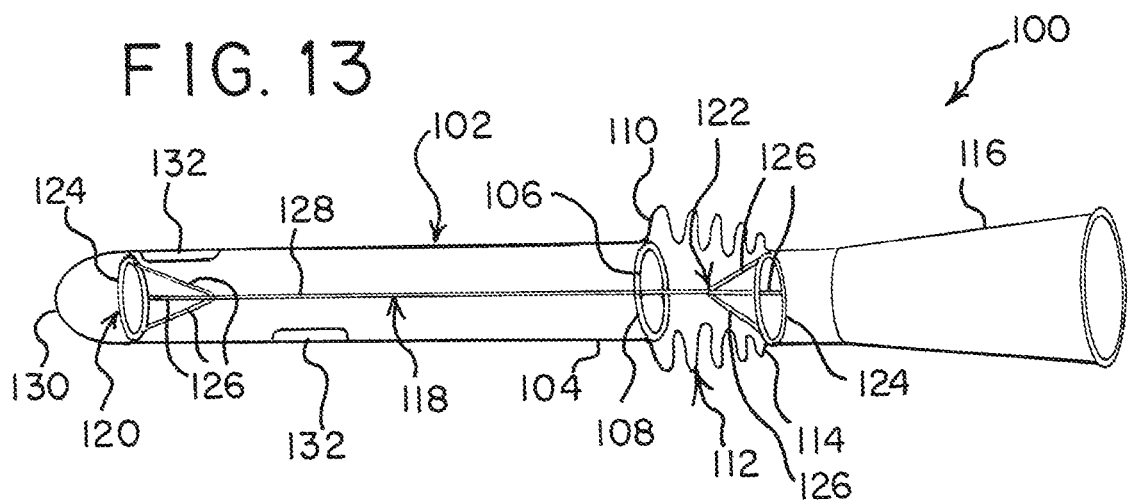
FIG. 13 is a front elevational view of another embodiment of a urinary catheter assembly in accordance with the present disclosure.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

FIG. 1 shows an embodiment of a urinary catheter assembly 10 according to an aspect of the present disclosure. The urinary catheter assembly 10 of FIG. 1 is configured for use by a male, but a urinary catheter assembly suitable for use by a female will also be described herein.

The urinary catheter assembly 10 includes a catheter member 12, which may be provided as an elongated, hollow tube extending between a proximal end 14 and a distal end 16. The catheter member 12 may be provided generally in accordance with a typical urinary catheter shaft (e.g., formed of the same or similar material and having the same or similar outer and inner diameters), but with a number of differences. For instance, a typical urinary catheter shaft may be provided with one or more drainage eyes or openings associated with the proximal end or proximal portion of the catheter shaft to allow urine from a bladder to flow into the hollow interior of the catheter shaft, where it flows to a drainage device (frequently provided as a funnel) to exit the catheter shaft. In contrast, the illustrated catheter member 12 includes at least one eye or opening 18 (shown as two) positioned at or adjacent to the proximal end 14 of the catheter member 12, along with at least one drainage eye or opening 20 (shown as two) positioned at or adjacent to the distal end 16 of the catheter member 12. Thus, whereas a typical urinary catheter shaft has differently configured proximal and distal ends, it will be seen that the proximal and distal ends 14 and 16 of the catheter member 12 of FIG. 1 are similarly configured (i.e., with a hemispherical end and one or more associated eyes or openings). While FIG. 1 illustrates a generally hemispherical distal end 16, the distal end 16 of the catheter member 12 may be differently configured without departing from the scope of the present disclosure, provided that the distal end 16 is sized and configured to be advanced into a male urethra U and drain urine from the hollow interior of the catheter member 12.

In addition to having a differently configured distal end 16, the catheter member 12 of FIG. 1 may also differ from typical urinary catheter shafts due to its length. In particular, a typical male urethra U may have a length on the order of approximately 20 cm, thereby requiring a catheter shaft that is at least that long to allow the catheter shaft to extend through the entire urethra U, with a proximal end of the catheter shaft positioned within the bladder B and a distal end of the catheter shaft (including the associated drainage device) positioned outside of the body. In contrast, the illustrated catheter member 12 is shorter than a typical urinary catheter shaft. By way of illustration, a typical urinary catheter assembly for use by a male may be on the order of approximately 40 cm long, whereas the urinary catheter assembly 10 of FIG. 1 may have a length on the order of approximately 20 cm in the compact configuration of FIG. 1. According to a method of using the urinary catheter assembly 10 (which will be described in greater detail), the entire catheter member 12 is positioned within the bladder/urethra (FIG. 3), traversing only a portion of the length of the urethra U, while other portions of the urinary catheter assembly 10 traverse the remaining portion of the urethra U and are positioned outside of the body to drain urine from the urinary catheter assembly 10.

The urinary catheter assembly 10 further includes a sleeve member 22. The axially compressible or deformable sleeve member 22 may be provided as a thin film or material formed into a tube (e.g., a lay flat tubing), with at least the distal end 16 of the catheter member 12 received within the sleeve member 22. In the illustrated embodiment, a proximal end 24 of the sleeve member 22 being secured to the outer surface of the catheter member 12 by a fluid-tight seal. The sleeve member 22 may be sealed to the catheter member 12 proximally of the distal eyes 20 (or whatever comparable drainage feature is provided at or adjacent to the distal end 16 of the catheter member 12) to allow urine to drain from the catheter member 12 into the sleeve member 22. Preferably, the proximal end 24 of the sleeve member 22 is sealed to the catheter member 12 just proximally of the distal eyes 20 (or comparable drainage feature), but it is also within the scope of the present disclosure for the sleeve member 22 to be secured to some other location of the catheter member 12. While the illustrated sleeve member 22 is secured to the outer surface of the associated catheter member 12, sleeve members according to the present disclosure may alternatively be secured to an inner surface of an associated catheter member having an open distal end.

The sleeve member 22 is configured to be more flexible than the catheter member 12, such as being sufficiently flexible to move between a bunched or pleated or folded condition when the urinary catheter assembly 10 is in a compact configuration (FIG. 1) to an elongated or extended condition in which there is a greater distance between the proximal and distal ends 24 and 26 of the sleeve member 22 (FIGS. 2 and 3). As shown in FIG. 3, at least a proximal portion of the sleeve member 22 is configured to be advanced into a urethra U during use of the urinary catheter assembly 10, such that it may be advantageous for the sleeve member 22 (or at least a proximal portion thereof) to be formed of a material suited for such use and/or for the sleeve member 22 (or at least a proximal portion thereof) to be treated with a coating that renders the coated portion of the sleeve member 22 suitable for temporary residence within a urethra U. In one embodiment, the outer surface of one or both of the catheter member 12 and the sleeve member 22 may be coated with a lubricious coating (which may comprise a hydrophilic or oleophilic substance, for example) to allow for easier advancement of the catheter member 12 and sleeve member 22 through the urethra U.

The distal end 26 of the sleeve member 22 may be associated with or secured to a drainage member 28. The drainage member 28 of FIGS. 1-3 is illustrated as a funnel provided generally in accordance with conventional design. The drainage member 28 is configured to remain outside of the body during use of the urinary catheter assembly 10 (as shown in FIGS. 2 and 3), so it may be formed of a generally rigid material, rather than being provided as a generally flexible or semi-rigid member. It also within the scope of the present disclosure for the drainage member 28 to be formed of a generally flexible or semi-rigid material, which may be advantageous when the drainage member 28 is used to hold a drainage bag connector. If the drainage member 28 is to be used in combination with a drainage bag, the drainage bag may be separately provided for connection to the drainage member 28 or may be pre-attached to define a closed system. Regardless of the material composition of the drainage member 28, the distal end 26 of the sleeve member 22 may be sealed around an outer perimeter of the drainage member 28 (e.g., to the outer surface of the cuff of the drainage member 28, if provided as a funnel) to direct urine from the sleeve member 22, to the drainage member 28, and then out of the urinary catheter assembly 10 for disposal in a waste location (e.g., a toilet or drainage bag). In other embodiments, the drainage member 28 may be differently configured and/or the sleeve member 22 may be differently associated with the drainage member 28.

The urinary catheter assembly 10 also includes a stylet 30. The stylet 30 extends between a proximal end 32, which is movably positioned within the hollow interior of the catheter member 12, and a distal end 34, which is positioned outside of the catheter member 12 and may be secured to the drainage member 28 (if provided). If a drainage member 28 is not provided, then the distal end 34 of the stylet 30 may be secured to the sleeve member 22 (e.g., at or adjacent to the distal end 26 of the sleeve member 22). During use of the urinary catheter assembly 10, the stylet 30 is advanced into the urethra U (FIG. 3), but it does not come into contact with the body (being positioned within the catheter member 12 and the sleeve member 22), so the material composition and surface treatment issues which inform the designs of the catheter member 12 and sleeve member 22 are not necessarily present for the stylet 30. It may be advantageous for the stylet 30 to be formed of a semi-rigid material (similar to the catheter member 12), which is sufficiently flexible to move between a generally straight or linear configuration (FIG. 1) to a curved or less linear configuration (FIG. 3) to allow the stylet 30 to move through the pathway defined by the urethra U. Additionally, as will be described in greater detail, the stylet 30 transmits a pushing force to the catheter member 12 in order to advance the urinary catheter assembly 10 through a urethra U, such that semi-rigidity (namely, a greater rigidity or stiffness than the catheter member 12) may be preferred to general flexibility to provide the stylet 30 with sufficient column strength to be pushed through the urethra U from its distal end 34 without buckling.

As will be described in greater detail, the stylet 30 allows for a telescoping urinary catheter assembly 10 having a variable length. However, it is also within the scope of the present disclosure for the stylet 30 itself to have a variable length (e.g., by the inclusion of a telescopic joint or hinge joint or the like), rather than having a fixed length. In an exemplary configuration employing a telescopic joint, the stylet may be comprised of two or more pieces and be movable between a compact configuration having a relatively short length (with at least one piece configured to be at least partially positioned within another piece, for example) and an elongated or extended configuration having a greater length (with said at least one piece of the stylet being moved at least partially out of said other piece to provide the increased length). If a telescopic stylet is provided, each of its two or more pieces may be configured to be locked together with the adjacent piece or pieces by any suitable locking mechanism to maintain the stylet in the elongated or extended configuration for use of the urinary catheter assembly. Similarly, a hinged joint may allow for two adjacent pieces of a stylet to be positioned side-by-side in a compact configuration and then moved to an elongated or extended configuration in which the two pieces are arranged end-to-end for an increased length. The provision of a variable length stylet may make it possible to further decrease the total length of the urinary catheter assembly in the compact configuration, while maintaining the same total length in the extended or elongated configuration, compared to a stylet having a fixed length. This allows for easier transportation of the urinary catheter assembly prior to use, while decreasing the amount of packaging required to contain the urinary catheter assembly and the amount of space the urinary catheter assembly occupies in a garbage can or other waste container.

The stylet 30 may have a proximal end 32 with a larger diameter than the portion 36 of the stylet 30 intermediate the proximal and distal ends 32 and 34. Such a configuration may be advantageous for retaining the proximal end 32 of the stylet 30 within the hollow interior of the catheter member 12. In particular, the distal end 16 of the catheter member 12 may include an opening or aperture 38 through which the intermediate portion 36 of the stylet 30 passes. In the illustrated embodiment, the opening 38 is centrally positioned at the distal end 16 of the catheter member 12 (i.e., at the location where a central axis of the catheter member 12 would intercept the distal end 16 of the catheter member 12), but the opening 38 may be positioned elsewhere without departing from the scope of the present disclosure.

Regardless of the location of the opening 38, it is preferably at least as large as the intermediate portion 36 of the stylet 30 (to allow the intermediate portion 36 to be movably received therein), while being smaller than the proximal end 32 of the stylet 30. By such a configuration, the stylet 30 may be moved with respect to the catheter member 12 without the two becoming dissociated (because the proximal end 32 of the stylet 30 cannot be moved distally out of the opening 38 at the distal end 16 of the catheter member 12). This effectively limits the range of motion of the stylet 30 with respect to the catheter member 12, as the stylet 30 is limited to movement between a position in which the proximal end 32 of the stylet 30 abuts the proximal end 14 of the catheter member 12 (FIG. 1) and a position in which the proximal end 32 of the stylet 30 abuts the distal end 16 of the catheter member 12 (FIGS. 2 and 3). The configuration of FIG. 1, in which the stylet 30 is in its most proximal position, with a distal portion of the stylet 30 positioned outside of the catheter member 12 (and at least partially within the sleeve member 22), is referred to herein as the compact configuration. The configuration of FIGS. 2 and 3, in which the stylet 30 is in its most distal position, with a larger distal portion of the stylet 30 positioned outside of the catheter member 12 (and at least partially within the sleeve member 22), is referred to herein as the elongated or extended configuration. The urinary catheter assembly 10 may be considered to be in an intermediate or transitional configuration when moving between the compact and extended configurations.

Preferably, some portion of the stylet 30 (e.g., its proximal end 32) and/or some portion of the catheter member 12 (e.g., its distal end 16) are configured to at least temporarily lock the proximal end 32 of the stylet 30 in place when the stylet 30 has moved to its most distal location (as shown in FIGS. 2 and 3). This may be achieved by an interference or friction fit between the proximal end 32 of the stylet 30 and the distal end 16 of the catheter member 12 or some other relationship (e.g., providing some portion of the stylet 30 with external threads that mate with internal threads of the catheter member 12 when the stylet 30 is in its most distal location) that temporarily or permanently locks the stylet 30 in place. A locking relationship between the stylet 30 and the catheter member 12 may also be provided to temporarily hold the stylet 30 in place when the stylet 30 has moved to its most proximal location (as shown in FIG. 1). This may be the initial position of the stylet 30, in which case there may be a weak adhesive bond between a portion of the stylet 30 (e.g., its proximal end 32) and a portion of the catheter member 12 (e.g., its proximal end 14) or some other temporary locking relationship between the stylet 30 and the catheter member 12 when the urinary catheter assembly 10 is initially provided to retain the urinary catheter assembly 10 in the compact configuration of FIG. 1. In other embodiments, rather than a locking relationship between a stylet and catheter member, a frictional fit therebetween may be sufficient, provided that the force required to dislodge the stylet from the catheter member in the extended configuration is greater than the insertion force required for catheterization.

In use, the urinary catheter assembly 10 (which may be provided in a sealed package or container) is moved from the compact configuration of FIG. 1 (in which the stylet 30 is in its most proximal location, with the proximal end 32 of the stylet 30 abutting or adjacent to the proximal end 14 of the catheter member 12) to the extended or elongated configuration of FIGS. 2 and 3 (in which the stylet 30 is in its most distal location, with the proximal end 32 of the stylet 30 abutting or adjacent to the distal end 16 of the catheter member 12). This may be achieved by gripping the catheter member 12 and a distal portion of the sleeve member 22 (or the drainage member 28, if provided) and moving them apart, with the catheter member 12 being moved in a proximal relative direction and the sleeve member 22 (or drainage member 28) being moved in a distal relative direction. If the catheter member 12 and stylet 30 are initially locked together, the lock therebetween is first overcome before moving the urinary catheter assembly 10 out of its compact configuration. Upon sufficient relative movement, the urinary catheter assembly 10 reaches the extended configuration, at which time the stylet 30 and catheter member 12 may be locked together (if a locking relationship is provided).

With the urinary catheter assembly 10 in the extended configuration, the proximal end 14 of the catheter member 12 may be advanced into a male urethra U and then advanced further through the urethra U. As described above, the stylet 30 preferably has sufficient column strength that a proximally directed force applied to the stylet 30 (e.g. by gripping the drainage member 28, if provided, and moving the drainage member 28 proximally) is transmitted to the catheter member 12 by the stylet 30. The catheter member 12 is advanced through the urethra U until the portion proximal of the sleeve member 22 is fully positioned within the urethra U (FIG. 2) and then further advanced to move the sleeve member 22 (with at least a portion of the stylet 30 positioned therein) into the urethra U. The urinary catheter assembly 10 may be further advanced through the urethra U until the proximal eyes 18 of the catheter member 12 are positioned within the bladder B. FIG. 3 illustrates this position with the drainage member 28 just distal of the urethral opening, but depending on the length of the urethra U, the proximal eyes 18 may reach the bladder B with the drainage member 28 farther spaced from the urethra U (e.g., with a larger portion of the sleeve member 22 and stylet 30 positioned outside of the urethra U).

As shown in FIG. 3, the catheter member 12 traverses a portion of the urethra U, while the sleeve member 22 (with a portion of the stylet 30 positioned therein) traverses the remainder of the urethra U. The exact dimensions of the individual components of the urinary catheter assembly 10 may vary without departing from the scope of the present disclosure, although it may be advantageous for the components to be sized and configured to conform to the anatomy of the male urethra U. For example, it may be advantageous for the catheter member 12 to be sized and configured to be positioned within the bladder neck N and external sphincter E of the urethra U (e.g., with a length no greater than approximately 15 cm), while the sleeve portion 22 and stylet 30 are sized and configured to be positioned within the bulbous urethra L and penile urethra P during use, as shown in FIG. 3. The bladder neck N and external sphincter E may require more radial strength to open than the bulbous urethra L and penile urethra P, which may be an advantage in providing the non-uniform strength design of the present disclosure, with a proximal portion (i.e., the catheter member 12) having a greater radial strength and a distal portion (i.e., the sleeve portion 22) having a lesser radial strength. In addition to having a non-uniform radial strength along its length, a urinary catheter assembly according to the present disclosure may also have a non-uniform flexural stiffness, with a more rigid distal portion (i.e., the stylet 30) providing pushability and a less rigid, more flexible proximal portion (i.e., the catheter member 12) providing low insertion force and comfort advantages.

With the urinary catheter assembly 10 in the position of FIG. 3, urine from the bladder B enters the hollow interior of the catheter member 12 via the proximal eyes 18 and flows through the catheter member 12 to the distal eyes 20. The urine flows out of the catheter member 12 via the distal eyes 20 and into the sleeve member 22. The urine travels the length of the sleeve member 22 to exit the urinary catheter assembly 10 at the distal end 26 of the sleeve member 22 or via the drainage member 28 (if provided). The urine may be emptied into a disposable bag or container associated with the urinary catheter assembly 10 or be directly drained into a waste container (e.g., a toilet). After use, the urinary catheter assembly 10 may be moved distally out of the urethra for disposal. The urinary catheter assembly 10 may be disposed of in its extended or elongated configuration (of FIGS. 2 and 3) or be returned to its initial compact configuration (of FIG. 1) to take up less space in a waste container.

While the foregoing method involves the urinary catheter assembly 10 being moved into its extended configuration prior to the catheter member 12 being advanced into a male urethra U, it is also within the scope of the present disclosure for the catheter member 12 to be at least partially advanced into the urethra U before being moved to the extended configuration. Other variations to the described method may also be practiced without departing from the scope of the present disclosure.

It should be understood that the configuration of the urinary catheter assembly 10 shown in FIGS. 1-3 is merely exemplary and that variations may be made to the illustrated design without departing from the scope of the present disclosure. For example, rather than having a generally linear configuration, the stylet 30 may be provided with a curved configuration (preferably while still providing a semi-rigid stylet that may be flexed into a generally linear configuration or different curved configuration). If the stylet 30 has a curved configuration, it may be rotated with respect to the catheter member during drainage of urine in order to direct the urine to the appropriate disposal location (e.g., into a toilet). In another embodiment, the sleeve member 22 may be formed using a water permeable material, in which case the space inside a package in which the urinary catheter assembly 10 is initially stored may be used as the vapor hydration source for a coating on the outer surface of the catheter member 12.

In an alternative embodiment, which may be practiced with any of the urinary catheter assemblies described herein (as well as other types of urinary catheters), a vapor hydration source may be positioned inside of the urinary catheter assembly 10 itself. In particular, a vapor hydration source (e.g., water) may be loaded into the urinary catheter assembly 10 (e.g., into the hollow interior of the catheter member 12 and/or sleeve member 22) during assembly. In an embodiment that includes a stylet 30 of the type described herein, it may be advantageous for the stylet 30 to create a temporary seal distal to the proximal eyes 18 and for the open distal end of the drainage member 28 to be provided with a removable seal to prevent leakage of the vapor hydration source prior to use. If the stylet 30 is not present or is present but does not form such a temporary seal, then an alternative approach may be provided to prevent leakage via the proximal eyes 18 (e.g., a fluid-tight, removable cover or cap or film or other seal may overlay the proximal eyes 18 and/or extend into the proximal eyes 18 to prevent fluid flow therethrough).

If provided, an internally located vapor hydration source may interact with a coating on the outer surface of the catheter member 12 (preferably while the urinary catheter assembly 10 is positioned within a sealed package) by passing vapor through a vapor-transmissive portion of the urinary catheter assembly 10. In one embodiment, all or a portion of the sleeve member 22 may be formed of a material that prevents the passage of the liquid (e.g., urine or a vapor hydration source in a liquid state), while allowing for vapor from the vapor hydration source to pass therethrough. Alternatively (or additionally), all or a portion of one or more of the other components of the urinary catheter assembly 10 (e.g., the catheter member 12, drainage member 28, and/or one of the seals/covers/caps associated with the proximal eyes 18 and/or drainage member 28) may be configured to allow for the passage of vapor therethrough to allow vapor from the internally located vapor hydration source to interact with a coating on the outer surface of the catheter member 12.

The internally located vapor hydration source keeps the coated portion of the catheter member 12 lubricated during storage and before use of the urinary catheter assembly 10. Just prior to use, the vapor hydration source may be removed from inside of the urinary catheter assembly 10 by any suitable approach (e.g., by removing a seal associated with the open distal end of the drainage member 28 and draining the vapor hydration source into a toilet or other waste receptacle). Then, with the internally located vapor hydration source removed from the urinary catheter assembly 10, the user may proceed to use the urinary catheter assembly 10 for catheterization as described above (or as described below for the other embodiments of the present disclosure).

FIGS. 4-7 illustrate another possible variation to the urinary catheter assembly design of FIGS. 1-3. In the embodiment of FIGS. 4-7, the urinary catheter assembly 40 is provided in accordance with the foregoing description of the urinary catheter assembly 10 of FIGS. 1-3, but further includes a gripper member 42. The gripper member 42 remains outside of the body during use (FIGS. 5-7), so it may be formed of one or more of any of a variety of suitable materials (e.g., a soft plastic material), without specific regard to lubricity.

The gripper member 42 may be generally tubular, with a hollow interior in which the distal end 16 of the catheter member 12 may be positioned when the urinary catheter assembly 40 is in the compact configuration of FIG. 4. In addition to surrounding the distal end 16 of the catheter member 12, the gripper member 42 may also surround a portion of the sleeve member 22, as shown in FIG. 4. It may be advantageous for the gripper member 42 to be distally movable with respect to the catheter member 12 (as will be described in greater detail) without being proximally movable with respect to the catheter member 12. As for the outer surface of the gripper member 42, it may be variously configured without departing from the scope of the present disclosure, although it may be advantageous for the outer surface of the gripper member to be contoured or otherwise configured for improved gripping and handling by a user (e.g., with raised ridges or ribs to prevent the digit of a user from slipping off of the gripper member 42 during use).

Regardless of its particular configuration, the gripper member 42 provides a location at which the urinary catheter assembly 40 may be gripped to move the urinary catheter assembly 40 from the compact configuration (FIG. 4) to the extended or elongated configuration (FIG. 5). In particular, rather than gripping a portion of the catheter member 12 when extending the urinary catheter assembly 40, the user may grip the gripper member 42 and the drainage member 28. The user may then move the gripper member 42 and drainage member 28 away from each other (pinching the gripper member 42 against the catheter member 12, as necessary) to move the stylet 30 distally with respect to the catheter member 12, as described above with respect to the embodiment of FIGS. 1-3. Thus, the gripper member 42 allows for a user to move the urinary catheter assembly 42 from its compact configuration to its extended or elongated configuration with a decreased risk of directly handling a portion of the urinary catheter assembly 40 that is advanced into the urethra U.

With the urinary catheter assembly 40 in its extended or elongated configuration, the gripper member 42 and/or drainage member 28 may be gripped while proximally advancing the catheter member 12 into the urethra U (FIG. 5). The catheter member 12 may be fully advanced until the gripper member 42 is positioned adjacent to the urethral opening (FIG. 7), at which time the gripper member 42 may be held in place while the drainage member 28 is moved proximally with respect to the gripper member 42. Such relative movement causes the sleeve member 22 and stylet 30 to move through the hollow interior of the gripper member 42 and into the urethra U, effectively advancing the gripper member 42 distally along the sleeve member 22 to be spaced distally of the distal end 16 of the catheter member 12. The drainage member 28 may be moved toward the gripper member 42 until the gripper member 42 contacts the drainage member 28 or until the proximal eyes 18 of the catheter member 12 are positioned within the bladder B. With the urinary catheter assembly 40 in the position of FIG. 6, urine may be drained from the bladder B, in accordance with the foregoing description of the embodiment of FIGS. 1-3. The drainage member 28 and/or the gripper member 42 may then be grasped and moved distally to withdraw the remainder of the urinary catheter assembly 40 from the urethra U.

FIGS. 8 and 9 illustrate another variation of the urinary catheter assembly 10 of FIGS. 1-3. In the embodiment of FIGS. 8 and 9, the urinary catheter assembly 44 includes a catheter member 12 and stylet 30, which may be provided generally in accordance with the above description of the catheter member 12 and stylet 30 of FIGS. 1-3. In addition to providing a substantially tubular sleeve member 46

(which may be referred to as a distal sleeve member in this embodiment), an additional proximal sleeve member 50 having a closed proximal end is also provided. The catheter member 12 is fully positioned within the sleeve members 46 and 50, with a proximal portion of the catheter member 12 positioned within the proximal sleeve member 50 and a distal portion of the sleeve member 12 positioned within the distal sleeve member 46 when the urinary catheter assembly 44 is in the compact configuration of FIG. 8. The sleeve members 46 and 50 may be formed of the same or different materials and/or with different surface treatments (e.g., with the proximal sleeve member 50 having a lubricious outer surface and the distal sleeve member 46 being non-lubricious).

Preferably, the proximal end of the proximal sleeve member 50 fits snugly over the proximal end 14 of the catheter member 12, with the proximal end of the proximal sleeve member 50 optionally being sealed or otherwise secured to the proximal end 14 of the catheter member 12 to prevent separation of the proximal ends of the proximal sleeve member 50 and the catheter member 12. By positioning the catheter member 12 fully within the sleeve members 46 and 50, the catheter member 12 does not come into contact with the urethra U or with the hand of the user during use of the urinary catheter assembly 44, allowing for a wider variety of materials to be used for the catheter member 12 and for less regard to surface treatment than a catheter member that directly contacts the urethra U.

As described above with regard to the catheter member 12 of FIGS. 1-3, the catheter member 12 of FIGS. 8 and 9 may be provided with one or more eyes or openings for allowing fluid into and out of the hollow interior of the catheter member 12. If the proximal end of the proximal sleeve member 50 is configured to overlay the proximal end 14 of the catheter member 12, it is advantageous for the proximal sleeve member 50 to be configured so as to not hinder the passage of urine from the bladder B into the hollow interior of the catheter member 12 via the proximal eyes 18. This may be achieved in any of a number of ways, such as by providing a proximal sleeve member 50 that has a perforated portion with holes or openings aligned with the proximal eyes 18 to allow fluid flow through the proximal eyes 18. Alternatively, the proximal sleeve member 50 may include a mesh portion or portions configured to overlay at least a portion of the proximal eyes 18. In yet another embodiment, rather than providing a proximal sleeve member 50 that overlays the proximal end 14 of the catheter member 12, a substantially tubular proximal sleeve member may be provided, with a proximal end of the sleeve member being secured or sealed to the catheter member 12 just distally of the proximal eyes 18, thereby allowing unhindered flow of urine through the proximal eyes 18.

The distal end 48 of the distal sleeve member 46 may be secured to a drainage member 52. The drainage member 52 of FIGS. 8 and 9 is illustrated as a generally annular structure with a through hole 54 for draining urine from the urinary catheter assembly 44. In other embodiments, the drainage member 52 may be differently configured, such as being configured as a funnel, as in FIGS. 1-7. The distal end 34 of the stylet 30 may also be secured to the drainage member 52, although it may be advantageous for the distal end 34 of the stylet 30 to be detachably secured to the drainage member 52 for reasons that will be described in greater detail herein.

The urinary catheter assembly 44 further includes an introducer tip 56, which extends between a distal end 58 and a proximal end 60, defining an interior chamber 62 therebetween. The proximal end 60 of the introducer tip 56 may be configured for insertion into a urethral opening prior to advancement of the catheter member 12 into the urethra U (as will be described). The proximal end 60 of the introducer tip 56 may include an aperture or opening 64 (FIG. 9) that may be moved between a closed configuration (in which there is no object positioned within the opening 64, as in FIG. 8) and an open configuration (in which the catheter member 12 or proximal sleeve member 50 and stylet 30 are partially positioned within or extending through the opening 64, with a portion of the object positioned within the introducer tip 56 and another portion positioned outside of the introducer tip 56, as in FIG. 9). In one embodiment, the proximal opening 64 is provided as a slit opening with one or more slits or cuts defining a plurality of deformable petals that may be moved to define the aforementioned open and closed configurations. In other embodiments, the opening 64 may be differently configured, provided that it is configured to allow passage of the catheter member 12, proximal sleeve member 50, and stylet 30 therethrough. The distal end 58 of the introducer tip 56 may be generally annular, with a central opening or passage through which the catheter member 12 and stylet 30 extend, with distal portions of the catheter member 12 and stylet 30 positioned outside of the interior chamber 62 in the compact configuration of FIG. 8. The distal end of the proximal sleeve member 50 may be secured to the distal end 58 of the introducer tip 56 (e.g., to a proximally facing surface of the distal end 58 so as to encircle the central opening), while the proximal end of the distal sleeve member 46 may also be secured to the distal end 58 of the introducer tip 56 (e.g., to a distally facing surface of the distal end 58 so as to encircle the central opening). Alternatively, the outer surface of one of the sleeve members may be secured to the inner surface of the other sleeve member, with the outer sleeve member being secured to the distal end 58 of the introducer tip 56 (e.g., along the perimeter of the central opening).

Proximal portions of the catheter member 12 and stylet 30, along with the entire proximal sleeve member 50 are positioned within the interior chamber 62 of the introducer tip 56 when the urinary catheter assembly 44 is in the compact configuration of FIG. 8. In use, a user grasps the introducer tip 56 and either advances the proximal end 60 of the introducer tip 56 into the urethra U or positions the proximal end 60 of the introducer tip 56 directly adjacent to the urethral opening. The user then applies a proximally directed force to the drainage member 52, which presses the proximal end 32 of the stylet 30 against the proximal end 14 of the catheter member 12. This proximally directed force urges the catheter member 12 out of the proximal opening 64 of the introducer tip 56 and into the urethra U. The proximal end 32 of the stylet 30 (which transmits the proximally directed force to the catheter member 12) and the proximal sleeve member 50 move along with the proximal end 14 of the catheter member 12 into the urethra U. Continued application of the proximally directed force to the drainage member 52 further advances the catheter member 12, proximal sleeve member 50, and stylet 30 into the urethra U.

Eventually, the distal end 34 of the stylet 30 and/or the proximal end of the drainage member 52 comes is brought into contact with the distal end 58 of the introducer tip 56. Preferably, the distal end 34 of the stylet 30 and/or the proximal end of the drainage member 52 is larger than the distal opening of the introducer tip 56, which prevents the distal end 34 of the stylet 30 and the drainage member 52 from advancing into the interior chamber 62 of the introducer tip 56. Preferably, the catheter member 12 and stylet 30 are configured such that the proximal eyes 18 of the catheter member 12 move into the bladder B before the distal end 34 of the stylet 30 or the proximal end of the drainage member 52 comes into contact with the distal end 58 of the introducer tip 56 (FIG. 9).

With the catheter member 12, proximal sleeve member 50, and stylet 30 so fully positioned within the urethra U (with the catheter member 12 received entirely within the proximal sleeve member 50), the drainage member 52 may be detached from the distal end 34 of the stylet 30. The manner in which the drainage member 52 is detached from the stylet 30 depends upon the connection between the drainage member 52 and the stylet 30 and may vary without departing from the scope of the present disclosure. By way of example, the drainage member 52 may be detached from the stylet 30 by distal movement of the drainage member 52 with respect to the stylet 30 or by rotation of the drainage member 52 with respect to the stylet 30. Detaching the drainage member 52 from the stylet 30 allows the drainage member 52 (along with the distal end 48 of the distal sleeve member 46) to be moved distally away from the introducer tip 56, as shown in FIG. 9. The drainage member 52 is moved to a convenient location (e.g., over a toilet or other disposal device) to direct urine out of the urinary catheter assembly 44.

Alternatively, rather than detaching the drainage member 52 from the stylet 30 after fully advancing the catheter member 12 and stylet 30 into the urethra U, the drainage member 52 may be detached from the stylet 30 earlier in the procedure and moved into position for drainage of urine prior to the proximal eyes 18 of the catheter member 12 being advanced into the bladder B. When practicing such a method, the distal end 34 of the stylet 30 may be grasped through the thin, flexible distal sleeve member 46 to proximally advance the stylet 30 (and, hence, the catheter member 12 and proximal sleeve member 50) through the urethra U, rather than advancing the urinary catheter assembly 44 through the urethra U by applying a proximally directed force to the drainage member 52.

FIGS. 10-12 illustrate another variation of the urinary catheter assembly 10 of FIGS. 1-3. The urinary catheter assembly 66 of FIGS. 10-12 includes a catheter member 68, sleeve member 70, stylet 72, and optional drainage member (not illustrated), which may be arranged and interconnected according to the above description of the urinary catheter assembly 10 of FIGS. 1-3. If the urinary catheter assembly 66 omits a drainage member (as shown), the distal end 74 of the sleeve member 70 may be secured to the distal end 76 of the stylet 72, with the distal end 76 of the stylet 72 having one or more holes or openings through which urine may be drained from the urinary catheter assembly 66. Otherwise, if the urinary catheter assembly 66 is provided with a drainage member (of the type illustrated in FIG. 1-6 or 8-9, for example), the distal ends 74 and 76 of the sleeve member 70 and stylet 72 may be fixedly secured to the drainage member rather than to each other. In other embodiments, the urinary catheter assembly 66 of FIGS. 10-12 may be provided with a gripper member and/or introducer tip of the type described above with respect to the embodiments of FIGS. 4-9.

A difference between the urinary catheter assembly 66 of FIGS. 10-12 and the urinary catheter assembly 10 of FIGS. 1-3 is that the urinary catheter assembly 66 of FIGS. 10-12 is designed and configured for use in a female urethra F, rather than a male urethra U. Accordingly, any one or more of the catheter member 68, the sleeve member 70, and the stylet 72 may be shorter than the corresponding component of the urinary catheter assembly 10 of FIGS. 1-3, on account of the female urethra F being shorter than the male urethra U. However, it is also within the scope of the present disclosure for any of the components of the female urinary catheter assembly 66 to be the same length or longer than the corresponding component of the male urinary catheter assembly 10 of FIGS. 1-3 or to otherwise be the same or differently sized (e.g., with a smaller or larger outer diameter) and/or shaped.

It will be seen that the stylet 30 of FIG. 1 is provided in a generally straight or linear initial configuration, while the stylet 72 of FIG. 10 is provided in a curved initial configuration. A generally straight or linear initial configuration is also possible for the stylet 72, although a curved configuration may be especially advantageous for the stylet 72 of a female urinary catheter assembly 66 according to the present disclosure to match the contours of the female urethra F. As noted above, male catheters according to the present disclosure may also be provided with an initial curved configuration. In comparison to the stylet 30 of the male urinary catheter assemblies described herein, the stylet 72 of the female urinary catheter assembly 66 may have the same rigidity, a greater rigidity, or a lesser rigidity without departing from the scope of the present disclosure.

In the illustrated embodiment, the proximal end 78 of the stylet 72 is positioned proximally of the proximal eyes 80 of the catheter member 68, such that applying a proximally directed force to the distal end 76 of the stylet 72 (either directly or through a drainage member associated with the stylet 72) will impart a proximally directed force to the proximal end 82 of the catheter member 68. Thus, by positioning the proximal end 82 of the catheter member 68 adjacent to the urethral opening and applying a proximally directed force to the stylet 72, the catheter member 68 will be advanced into and through the urethra F to the position of FIG. 11. From the position of FIG. 11, the stylet 72 may be moved distally with respect to the catheter member 68 (which remains in place within the urethra F) to move the urinary catheter assembly 66 from a compact configuration (FIGS. 10 and 11) to an extended or elongated configuration (FIG. 12), in which a greater portion of the stylet 72 is positioned outside of the catheter member 68 and within the sleeve member 70. The distal ends 74 and 76 of the sleeve member 70 and stylet 72, now positioned farther from the distal end 84 of the catheter member 68, may be repositioned by rotating the stylet 72 with respect to the catheter member 68. This may be advantageous depending on the environment in which the urinary catheter assembly 66 is being used. For example, if urine is to be drained into a toilet, then it may be preferred to orient the distal ends 74 and 76 of the sleeve member 70 and stylet 72 backwards, whereas it may be preferred to orient the distal ends 74 and 76 of the sleeve member 70 and stylet 72 forwards for drainage into a receptacle if the urinary catheter assembly 66 is being used while in a chair.

It should be understood that the illustrated configuration of the female urinary catheter assembly 66 is merely exemplary and that variations may be made to the illustrated design without departing from the scope of the present disclosure. For example, rather than having the proximal end 78 of the stylet 72 positioned proximally of the proximal eyes 80 of the catheter member 68 in the compact (insertion) configuration (as shown in FIG. 10), the stylet 72 and the catheter member 68 may be configured so as to position the proximal end 78 of the stylet 72 distally of the proximal eyes 80. Preferably, if the proximal end 78 of the stylet 72 is positioned distally of the proximal eyes 80, it is only positioned a short distance distally of the proximal eyes 80

(e.g., much closer to the proximal eyes 80 than to the distal eyes 86) to avoid increasing the length of the urinary catheter assembly 66 in the compact configuration. In another embodiment, a proximal portion of the sleeve member 70 may be configured to be advanced into the urethra F during use.

By initially positioning the proximal end 78 of the stylet 72 distally of the proximal eyes 80, the proximal end 78 may act as a plug (by being sized and configured to press against the inner wall of the catheter member 68), which prevents the flow of urine through the catheter member 68 when the proximal eyes 80 are positioned within the bladder B. With the proximal eyes 80 positioned within the bladder B, the stylet 72 may be moved distally with respect to the catheter member 68 until the proximal end 78 of the stylet 72 is positioned distally of the distal eyes 86 of the catheter member 68 (as in FIG. 12). Moving the proximal end 78 of the stylet 72 distally beyond the distal eyes 86 effectively "unplugs" or opens fluid flow through the catheter member 68, from the proximal eyes 80 to the distal eyes 86, into the sleeve member 70, and then out of the urinary catheter assembly 66 via an opening in the distal end 76 of the stylet 72 (or via a drainage member associated with the distal end 76 of the stylet 72, if provided). As the proximal end 78 of the stylet 72 does not contact the proximal end 82 of the catheter member 68 in the compact configuration, a proximally directed force applied to the distal end 76 of the stylet 72 (or to an associated drainage member, if provided) may press against the distal end 84 of the catheter member 68 (or press the folded or bunched sleeve member 70 against the distal end 84 of the catheter member 68) to advance the catheter member 68 into and through the urethra F during insertion.

Any of a number of variations may be made to the configurations of the catheter assemblies described herein. For example, while all of the catheter members illustrated herein include a plurality of drainage eyes defined in the tubular wall of the distal portion of catheter member, it is within the scope of the present disclosure for a drainage eye to be located at the distal end of the catheter member. For example, a catheter member according to the present disclosure may be provided with a distal portion having an "open-ended" design. FIG. 13 illustrates one embodiment of a urinary catheter assembly 100 having an "open-ended" catheter member 102. The illustrated "open-ended" catheter member 102 has a distal portion 104 that is substantially tubular (rather than having a generally hemispherical end), with a drainage eye or opening 106 at the distal end 108 of the catheter member 102. It should be understood that the configuration of FIG. 13 is merely exemplary and that the distal portion of an "open-ended" catheter member may be differently configured (e.g., with a generally hemispherical distal end including a drainage opening) without departing from the scope of the present disclosure.

Similar to the previously described embodiments, the catheter member 102 (e.g., the distal portion 104 or distal end 108 of the catheter member 102) may be sealed to the proximal end or portion 110 of a sleeve member 112, with a distal end or portion 114 of the sleeve member 112 being sealed to a drainage member 116 (if provided).

If the catheter member has an "open-ended" design, it may be advantageous to also modify the configuration of the associated stylet, although it is also within the scope of the present disclosure for a stylet of the type described above to be used in combination with an "open-ended" catheter member (or for a stylet of the type illustrated in FIG. 13 to be used in combination with any of the catheter members described herein). In the illustrated embodiment, the stylet 118 is "open-ended," with proximal and distal ends 120 and 122 each configured as a conical cage that defines one or more openings or passages that allow for urine to flow through (rather than around) the end of the stylet 118. Each illustrated end 120, 122 comprises a rim 124 with a plurality of extensions or arms 126 connecting the rim 124 to an intermediate or central portion 128 of the stylet 118. The rim 124 has a relatively large diameter (compared to the intermediate portion 128 of the stylet 118), but (at least the rim 124 of the proximal end 120) is preferably sized to fit within the hollow interior of the catheter member 102 for sliding movement within the catheter member 102. The proximal and distal ends 120 and 122 may be differently configured, for example with one being "open" (allowing urine flow through the end) and the other being "closed" (allowing urine flow around the end), or with differently configured "open" designs, such as a distal end 122 that is configured to remain outside of the catheter member 102 and may, therefore, have a rim 124 with a larger diameter than the rim 124 of the proximal end 120. The distal end 122 is preferably fixedly secured to the drainage member 116, but it may alternatively be removably secured to the drainage member 116. It is also within the scope of the present disclosure for the exact configuration of the open end of a stylet to vary from the conical cage design of FIG. 13, provided that the open end is configured to allow for urine flow through the end of the stylet.

Other than urine flowing through the ends 120 and 122 of the stylet 118 (rather than around the ends) and into the sleeve member 112 from a drainage opening 106 at the distal end 108 of the catheter member 102 (rather than through distal drainage openings in the tubular wall), a urinary catheter assembly 100 of the type shown in FIG. 13 may be used in accordance with the above-described methods to catheterize a male or female. In one exemplary method of use, the urinary catheter assembly 100 (which may be provided in a sealed package or container) is moved from the compact configuration of FIG. 13 to an extended or elongated configuration (in which the stylet 118 is in its most distal location, with the proximal end 120 of the stylet 118 abutting or adjacent to the distal end 108 of the catheter member 102).

With the urinary catheter assembly 100 in the extended configuration, the proximal end 130 of the catheter member 102 may be advanced into a urethra and then advanced further through the urethra. The catheter member 102 is advanced through the urethra until its proximal drainage openings 132 are positioned within the bladder, typically with at least a portion of the stylet 118 and sleeve member 112 positioned within the urethra and the drainage member 116 positioned outside of the urethra.

With the urinary catheter assembly so positioned, urine from the bladder enters the hollow interior of the catheter member 102 via the proximal eyes 132 and flows through the catheter member 102 (passing through the open proximal end 120 of the stylet 118) to the distal drainage opening 106. The urine flows out of the catheter member 102 via the distal drainage opening 106 and into the sleeve member 112. The urine travels the length of the sleeve member 112, ultimately passing through the open distal end 122 of the stylet 118 to exit the urinary catheter assembly 100 via the drainage member 116. The urine may be emptied into a disposable bag or container associated with the urinary catheter assembly 100 or be directly drained into a waste container (e.g., a toilet). After use, the urinary catheter assembly 100 may be moved distally out of the urethra for disposal. The urinary catheter assembly 100 may be disposed of in its extended or elongated configuration or be returned to its initial compact configuration (of FIG. 13) to take up less space in a waste container. It should be understood that this method of use is merely exemplary and that other methods of use (including ones in which the urinary catheter assembly 100 is at least partially advanced into the urethra in its compact configuration) may be practiced without departing from the scope of the present disclosure.

Figure 14:
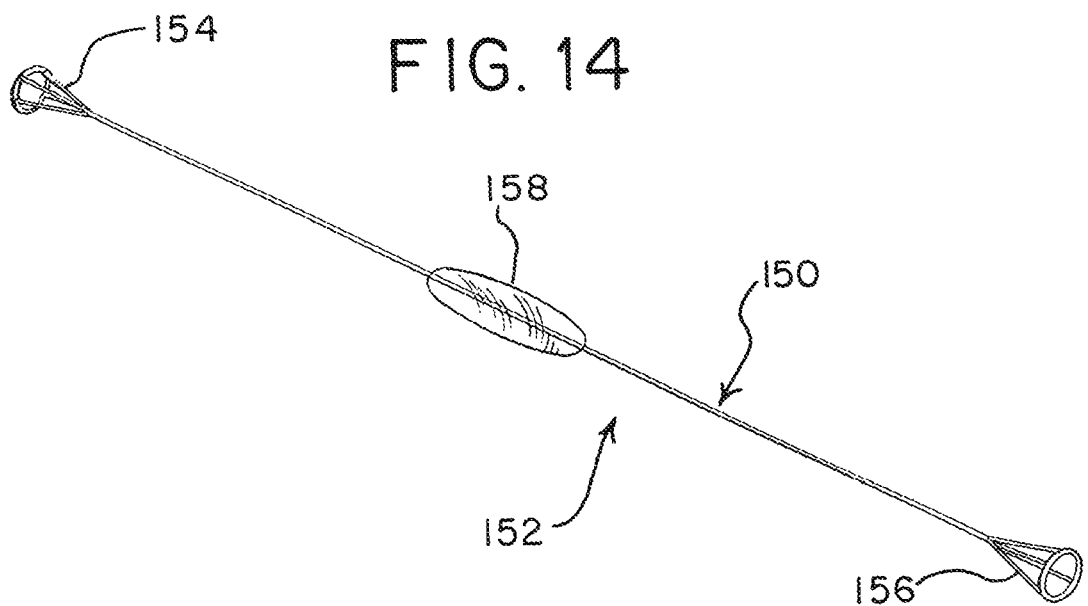
FIG. 14 is a front elevational view of an alternative embodiment of a stylet suitable for use in a urinary catheter assembly according to the present disclosure.

FIG. 14 illustrates a variation of the open-ended stylet 118 of FIG. 13. In the embodiment of FIG. 14, an intermediate portion 150 of the stylet 152 between the proximal and distal ends 154 and 156 includes a support formation 158. The support formation 158 has a larger diameter than the remainder of the intermediate portion 150 of the stylet 152 (but preferably smaller than the diameter of the proximal end 154 of the stylet 152) and may be variously configured for improved gripping and handling of the stylet 152 through an associated sleeve member, while also preventing collapse of the sleeve member (which could hinder urine flow). It should be understood that a stylet incorporating a support formation is not limited to open-ended stylets, but that any stylet according to the present disclosure may be provided with a support formation.

Figure 15:
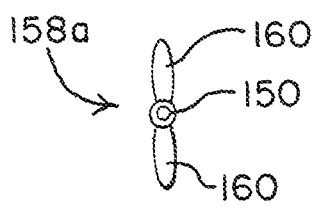
FIGS. 15-17 illustrate alternative cross-sectional shapes of a support formation of the stylet of FIG. 14.
Figure 16:
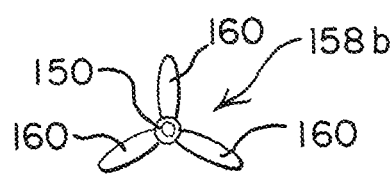
Figure 17:
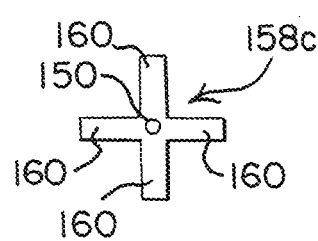

FIGS. 15-17 illustrate exemplary cross-sectional shapes of the support formation 158a-158c, having two petals or extensions 160 (FIG. 15), three petals or extensions 160 (FIG. 16), or four petals or extensions 160 (FIG. 17), but it should be understood that the support formation 158 may have a single extension or more than four extensions. The illustrated petals or extensions 160 of each embodiment are substantially identical and may be symmetrically spaced apart from the adjacent extension(s) 160, but it is within the scope of the present disclosure for them to be differently configured and/or to be non-uniformly spaced from each other. Additionally, more than one support formation 158 may be spaced along the length of the intermediate portion 150 of the stylet 152, with the support formations being substantially identical or differently configured. Furthermore, the length of an individual support formation 158 may vary from what is illustrated in FIG. 14 (e.g., occupying a larger or smaller percentage of the length of the intermediate portion 150 of the stylet 152) and/or an individual support formation 158 may be positioned at a different location relative to the ends 154 and 156 (e.g., positioned closer to one end than the other, rather than being substantially centered) without departing from the scope of the present disclosure.

FIGS. 18 and 19 illustrate a package 200 that may be used in combination with any of the urinary catheter assemblies described herein, but may have particular utility when used in combination with a urinary catheter assembly omitting a gripper member. The illustrated package 200 has proximal and distal portions 202 and 204 that are joined at a frangible section 206, such as a tear strip. A urinary catheter assembly 208 is positioned within the package 200, with a proximal portion (which may include the catheter member 210) received within the proximal portion 202 of the package 200 and a distal portion (which may include the drainage member 212) received within the distal portion 204 of the package 200 (FIG. 18) when the package 200 is intact and sealed.

In use, the frangible section 206 of the package 200 is broken (e.g., by moving the two portions 202 and 204 of the package 200 apart or pulling a tear strip). Gripping the urinary catheter assembly 208 through the package 200 (by pinching the proximal portion 202 of the package 200 against the catheter member 210 and pinching the distal portion 204 of the package 200 against the drainage member 212), the separated portions 202 and 204 of the package 200 may be moved apart to move the urinary catheter assembly 208 from the compact configuration of FIG. 18 to the extended or elongated configuration of FIG. 19 (or to an at least partially extended configuration). By such an arrangement, the urinary catheter assembly 208 may be initially provided in its compact configuration (to reduce the amount of packaging required) and moved to its extended configuration for use without directly handling the catheter member 210, which may be especially advantageous if the urinary catheter assembly 208 is provided without a gripper member.

Alternatively, rather than requiring a user to grip the urinary catheter assembly 208 through the package 200, a retention member or mechanism may be incorporated into one or both portions 202 and 204 of the package 200. The retention member or mechanism (e.g., a weak adhesive bond) releasably connects the urinary catheter assembly 208 to the package 200, such that separated portions 202 and 204 of the package 200 may be gripped and moved apart (without gripping the urinary catheter assembly 208 through the package 200) to move the urinary catheter assembly 208 to its extended configuration. Once the urinary catheter assembly 208 reaches its extended configuration, additional movement of the portions 202 and 204 of the package 200 away from each other will cause the retention member or mechanism to fail or detach or release, thereby disconnecting the urinary catheter assembly 208 from the package 200 for use. While it may be advantageous for the package 200 to be involved in moving the urinary catheter assembly 208 to its extended configuration, it is also within the scope of the present disclosure for the urinary catheter assembly 208 to be removed from the package 200 while still in its compact configuration.

FIGS. 20 and 21 illustrate a variation of a urinary catheter assembly 250 incorporating a stylet 252. Similar to the embodiment of FIG. 13, the urinary catheter assembly 250 of FIGS. 20 and 21 includes a catheter member 254 that is connected to a drainage member 256 by a generally tubular sleeve member 258, with an open-ended stylet 252 positioned within the sleeve member 258. However, in contrast to the foregoing embodiments, the proximal end 260 of the stylet 252 is not configured to move within the hollow interior of the catheter member 254, but is instead fixedly secured at or adjacent to the distal end 262 of the catheter member 254. The distal end 264 of the stylet 252 is fixedly secured to the drainage member 256, meaning that the urinary catheter assembly 250 of FIGS. 20 and 21 is not telescopic, but instead has a fixed length.

While the urinary catheter assembly 250 has a fixed length, it is still capable of being moved between a compact configuration and an extended or elongated configuration. FIG. 21 shows the urinary catheter assembly 250 in a compact configuration (within a package 266), with the urinary catheter assembly 250 being folded or bent onto itself (placing the proximal end 268 of the catheter member 254 adjacent to the drainage member 256) for improved portability prior to use. This is possible by providing a deformable stylet 252, which may be flexed or folded or otherwise deformed from a generally straight or linear configuration (FIG. 20) to a less straight or linear configuration (FIG. 21). While the stylet 250 of FIGS. 20 and 21 has a generally linear configuration, it is also within the scope of the present disclosure for the stylet 252 to have a generally curved configuration (as in the embodiment of FIGS. 10-12), in which case the stylet may be moved from the generally curved configuration to a more curved, compact configuration. Preferably, the stylet 252 is formed of a resiliently or elastically deformable material (as opposed to a plastically deformable material) to allow the stylet 252 to move between its compact and elongated configurations without kinking or becoming permanently deformed or otherwise deviating from its intended elongated configuration.

Although the urinary catheter assembly 250 of FIGS. 20 and 21 is not telescopic, it retains the same advantages as a telescopic urinary catheter assembly during use. In particular, the urinary catheter assembly 250 provides a variable-stiffness assembly in the elongated configuration, with a relatively soft or pliable proximal section (i.e., the catheter member 254) for improved movement through a urethra and a more rigid or stiffer distal section (i.e., the stylet 252 within the sleeve member 258) for improved pushability.

Aspects of the present subject matter described above may be beneficial alone or in combination with one or more other aspects. Without limiting the foregoing description, in accordance with one aspect of the subject matter herein, there is provided a urinary catheter assembly, which includes a catheter member, a sleeve member, and a stylet. The sleeve member receives at least a portion of the catheter member and has a greater flexibility than the catheter member. The stylet includes a proximal end movably positioned within the catheter member and a distal portion positioned outside of the catheter member, with the urinary catheter assembly being movable between a compact configuration and an extended configuration.

In accordance with another aspect which may be used or combined with the preceding aspect, the distal portion of the stylet is positioned outside of the catheter member and at least partially within the sleeve member when the urinary catheter assembly is in the compact configuration. A larger distal portion of the stylet is positioned outside of the catheter member when the urinary catheter assembly is in the extended configuration.

In accordance with another aspect which may be used or combined with any of the preceding aspects, the sleeve member includes a proximal end secured to the catheter member.

In accordance with another aspect which may be used or combined with any of the preceding aspects, the proximal end of the stylet has a larger diameter than an intermediate portion of the stylet.

In accordance with another aspect which may be used or combined with any of the preceding aspects, there is provided a drainage member, with the sleeve member including a distal end secured to the drainage member and the stylet including a distal end secured to the drainage member.

In accordance with another aspect which may be used or combined with any of the preceding aspects, there is provided a gripper member, which surrounds a distal end of the catheter member in the compact configuration and is spaced distally of the distal end of the catheter member in the extended configuration.

In accordance with another aspect which may be used or combined with any of the first five aspects, there is provided an introducer tip defining an interior chamber between proximal and distal ends of the introducer tip and a proximal sleeve member positioned within the interior chamber of the introducer tip in the compact configuration. A proximal portion of the catheter member is positioned within the interior chamber and a distal portion of the catheter member is positioned outside of the interior chamber in the compact configuration, with the sleeve member being positioned outside of the interior chamber.

In accordance with another aspect which may be used or combined with the immediately preceding aspect, the proximal sleeve member receives the proximal portion of the catheter member and the sleeve member receives the distal portion of the catheter member in the compact configuration.

In accordance with another aspect which may be used or combined with any of the preceding two aspects, there is provided a drainage member, with the sleeve member including a distal end secured to the drainage member and the stylet including a distal end detachably secured to the drainage member.

In accordance with another aspect which may be used or combined with any of the preceding aspects, the stylet has a curved configuration.

In accordance with another aspect which may be used or combined with any of the preceding aspects, the stylet is rotatable with respect to the catheter member.

In accordance with another aspect which may be used or combined with any of the preceding aspects, the catheter member includes proximal and distal ends, with at least one proximal drainage eye positioned at or adjacent to the proximal end of the catheter member and at least one distal drainage eye positioned at or adjacent to the distal end of the catheter member.

In accordance with another aspect which may be used or combined with any of the preceding aspects, the stylet extends between proximal and distal ends, with at least one of the ends of the stylet being configured to allow fluid flow through at least one of the ends of the stylet.

In accordance with another aspect which may be used or combined with any of the preceding aspects, the stylet includes a support formation associated with an intermediate portion of the stylet and having a larger diameter than the remainder of the intermediate portion.

In accordance with another aspect, there is provided a method for using a urinary catheter assembly. The method includes providing a urinary catheter assembly including a catheter member, a sleeve member receiving at least a portion of the catheter member, and a stylet including a proximal end movably positioned within the catheter member and a distal portion positioned outside of the catheter member and at least partially within the sleeve member. The stylet is moved distally with respect to the catheter member to position a larger distal portion of the stylet outside of the catheter member. A proximal end of the catheter member is advanced into a urethra until the proximal end of the catheter member is positioned within a bladder, with at least a distal end of the sleeve member and a distal end of the stylet positioned outside of the urethra.

In accordance with another aspect which may be used or combined with the immediately preceding aspect, providing a urinary catheter member includes providing the sleeve member with a proximal end secured to the catheter member.

In accordance with another aspect which may be used or combined with any of the preceding two aspects, providing a urinary catheter member includes providing the proximal end of the stylet with a larger diameter than an intermediate portion of the stylet.

In accordance with another aspect which may be used or combined with any of the preceding three aspects, providing a urinary catheter assembly includes providing the urinary catheter assembly with a drainage member secured to distal ends of the sleeve member and the stylet.

In accordance with another aspect which may be used or combined with the immediately preceding aspect, advancing a proximal end of the catheter member into a urethra includes gripping the drainage member and moving the drainage member proximally to advance the proximal end of the catheter member through the urethra.

In accordance with another aspect which may be used or combined with any of the preceding five aspects, providing a urinary catheter assembly includes providing the urinary catheter assembly with a gripper member associated with the catheter member.

In accordance with another aspect which may be used or combined with the immediately preceding aspect, advancing a proximal end of the catheter member into a urethra includes gripping the gripper member when advancing the proximal end of the catheter member into the urethra.

In accordance with another aspect which may be used or combined with any of the preceding two aspects, advancing a proximal end of the catheter member into a urethra includes moving the gripper member distally with respect to the sleeve member when advancing the proximal end of the catheter member through the urethra.

In accordance with another aspect which may be used or combined with any of the fifteenth through nineteenth aspects, providing a urinary catheter assembly includes providing the urinary catheter assembly with an introducer tip defining an interior chamber between proximal and distal ends of the introducer tip, with proximal portions of the catheter member and the sleeve member positioned within the interior chamber and distal portions of the catheter member and the sleeve member positioned outside of the interior chamber.

In accordance with another aspect which may be used or combined with the immediately preceding aspect, advancing a proximal end of the catheter member into a urethra includes proximally advancing the proximal end of the catheter member out of the interior chamber and into a urethra via the proximal end of the introducer tip, with the sleeve member being retained on the catheter member and a portion of the sleeve member exiting the interior chamber with the proximal end of the catheter member.

In accordance with another aspect which may be used or combined with any of the preceding two aspects, providing a urinary catheter assembly includes providing the urinary catheter assembly with a drainage member secured to distal ends of the sleeve member and the stylet, with the method further including detaching the distal end of the stylet from the drainage member.

In accordance with another aspect which may be used or combined with any of the preceding eleven aspects, providing a urinary catheter assembly includes providing the urinary catheter assembly with the stylet having a curved configuration.

In accordance with another aspect which may be used or combined with any of the preceding twelve aspects, the stylet is rotated with respect to the catheter member after moving the stylet distally with respect to the catheter member.

In accordance with another aspect which may be used or combined with any of the preceding thirteen aspects, moving the stylet distally with respect to the catheter member is performed before advancing a proximal end of the catheter member into a urethra.

In accordance with another aspect which may be used or combined with any of the fifteenth through twenty-seventh aspects, moving the stylet distally with respect to the catheter member is performed after advancing a proximal end of the catheter member into a urethra.

In accordance with another aspect which may be used or combined with the fifteenth aspect, providing a urinary catheter assembly includes providing a urinary catheter assembly received within a package, and moving the stylet distally with respect to the catheter member includes gripping two portions of the urinary catheter assembly through the package and moving the two portions of the urinary catheter assembly apart to position a larger distal portion of the stylet outside of the catheter member.

In accordance with another aspect, there is provided a urinary catheter assembly including a catheter member, a drainage member, a sleeve member, and a stylet. The sleeve member is secured to the catheter member and the drainage member, while the stylet is positioned within the sleeve member and includes a proximal end secured to the catheter member and a distal end secured to the drainage member.

In accordance with another aspect which may be used or combined with the immediately preceding aspect, the stylet is deformable to move the urinary catheter assembly between a compact configuration and an extended configuration.

In accordance with another aspect which may be used or combined with any of the preceding two aspects, the stylet extends between proximal and distal ends, with at least one of the ends of the stylet being configured to allow fluid flow through at least one of the ends of the stylet.

In accordance with another aspect which may be used or combined with any of the preceding three aspects, the stylet includes a support formation associated with an intermediate portion of the stylet and having a larger diameter than the remainder of the intermediate portion.

In accordance with another aspect, there is provided a urinary catheter assembly including a catheter member defining an interior, with a vapor hydration source positioned within the interior of the catheter member. The catheter member includes at least one vapor-transmissive portion configured to allow passage of vapor from the vapor hydration source from the interior of the catheter member and prevent passage of the vapor hydration source. The catheter member also includes an external coating configured to become lubricious upon exposure to vapor from the vapor hydration source.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A urinary catheter assembly, comprising:
   a catheter member;
   a sleeve member secured to the catheter member and having a greater flexibility than the catheter member; and
   a stylet extending between proximal-most and distal-most ends, with the proximal-most end being irremovably positioned within the catheter member and a distal portion of the stylet being irremovably positioned within the sleeve member, wherein the urinary catheter assembly is movable between a compact configuration in which the proximal-most end of the stylet is positioned adjacent to a proximal end of the catheter member and an extended configuration in which the proximal-most end of the stylet is positioned farther from the proximal end of the catheter member, the urinary catheter assembly has a greater length than in the compact configuration, and the proximal-most end of the stylet is at least temporarily locked in place within the catheter member.

2. The urinary catheter assembly of claim 1, wherein
the distal portion of the stylet is positioned outside of the catheter member and at least partially within the sleeve member when the urinary catheter assembly is in the compact configuration, and
a larger distal portion of the stylet is positioned outside of the catheter member when the urinary catheter assembly is in the extended configuration.

3. The urinary catheter assembly of claim 1, wherein the proximal-most end of the stylet has a larger diameter than an intermediate portion of the stylet.

4. The urinary catheter assembly of claim 1, further comprising a drainage member, wherein the sleeve member includes a distal end secured to the drainage member and the distal-most end of the stylet is secured to the drainage member.

5. The urinary catheter assembly of claim 1, further comprising a gripper member surrounding a distal end of the catheter member in the compact configuration and spaced distally of the distal end of the catheter member in the extended configuration.

6. The urinary catheter assembly of claim 1, further comprising an introducer tip defining an interior chamber between proximal and distal ends of the introducer tip and a proximal sleeve member positioned within the interior chamber of the introducer tip in the compact configuration, wherein
a proximal portion of the catheter member is positioned within the interior chamber and a distal portion of the catheter member is positioned outside of the interior chamber in the compact configuration, and
the sleeve member is positioned outside of the interior chamber.

7. The urinary catheter assembly of claim 6, wherein the proximal sleeve member receives the proximal portion of the catheter member and the sleeve member receives the distal portion of the catheter member in the compact configuration.

8. The urinary catheter assembly of claim 6, further comprising a drainage member, wherein the sleeve member includes a distal end secured to the drainage member and the distal-most end of the stylet is detachably secured to the drainage member.

9. The urinary catheter assembly of claim 1, wherein the stylet has a curved configuration.

10. The urinary catheter assembly of claim 1, wherein the stylet is rotatable with respect to the catheter member.

11. The urinary catheter assembly of claim 1, wherein at least one of the ends of the stylet is configured to allow fluid flow through said at least one of the ends of the stylet.

12. The urinary catheter assembly of claim 1, wherein the stylet includes a support formation associated with an intermediate portion of the stylet and having a larger diameter than the remainder of the intermediate portion.

13. A method of using a urinary catheter assembly including a catheter member, a sleeve member secured to the catheter member, and a stylet extending between proximal-most and distal-most ends, with the proximal-most end being irremovably positioned within the catheter member adjacent to a proximal end of the catheter member and a distal portion of the stylet being irremovably positioned within the sleeve member, the method comprising:
moving the stylet distally with respect to the catheter member to position the proximal-most end of the stylet farther from the proximal end of the catheter member and to position a larger distal portion of the stylet within the sleeve member, thereby increasing the length of the urinary catheter assembly, with the proximal-most end of the stylet at least temporarily locked in place within the catheter member; and
advancing the proximal end of the catheter member into a urethra until the proximal end of the catheter member is positioned within a bladder, with at least a distal end of the sleeve member and the distal-most end of the stylet positioned outside of the urethra.

14. The method of claim 13, wherein said moving the stylet distally with respect to the catheter member is performed before said advancing the proximal end of the catheter member into a urethra.

15. The method of claim 13, wherein said moving the stylet distally with respect to the catheter member is performed after said advancing the proximal end of the catheter member into a urethra.

16. The method of claim 13, wherein
the urinary catheter assembly is received within a package, and
said moving the stylet distally with respect to the catheter member includes gripping two portions of the urinary catheter assembly through the package and moving said two portions of the urinary catheter assembly apart to position a larger distal portion of the stylet outside of the catheter member.

17. A urinary catheter assembly, comprising:
a catheter member extending between a proximal end and a distal end;
a drainage member;
a sleeve member secured to the catheter member and the drainage member and configured to be at least partially advanced into a urethra; and
a stylet positioned within the sleeve member and including a proximal-most end secured at or adjacent to the distal end of the catheter member and a distal-most end secured to the drainage member, wherein the proximal-most end of the stylet is irremovably secured to the catheter member and the distal-most end of the stylet is irremovably positioned within the sleeve member.

18. The urinary catheter assembly of claim 17, wherein the stylet is deformable to move the urinary catheter assembly between a compact configuration and an extended configuration.

19. The urinary catheter assembly of claim 17, wherein at least one of the ends of the stylet is configured to allow fluid flow through said at least one of the ends of the stylet.

20. The urinary catheter assembly of claim 17, wherein the stylet includes a support formation associated with an intermediate portion of the stylet and having a larger diameter than the remainder of the intermediate portion.

* * * * *